United States Patent
Suzuki et al.

(10) Patent No.: US 12,054,468 B2
(45) Date of Patent: Aug. 6, 2024

(54) COMPOUND, COMPOSITION, CURED PRODUCT, OPTICALLY ANISOTROPIC BODY, AND REFLECTIVE FILM

(71) Applicant: FUJIFILM Corporation, Tokyo (JP)

(72) Inventors: Yuko Suzuki, Minami-ashigara (JP); Keisuke Kodama, Minami-ashigara (JP); Shunya Katoh, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 757 days.

(21) Appl. No.: 17/193,394

(22) Filed: Mar. 5, 2021

(65) Prior Publication Data

US 2021/0198230 A1 Jul. 1, 2021

Related U.S. Application Data

(63) Continuation of application No. PCT/JP2019/031630, filed on Aug. 9, 2019.

(30) Foreign Application Priority Data

Sep. 6, 2018 (JP) .................................. 2018-167217

(51) Int. Cl.
| | | |
|---|---|---|
| *C07D 321/10* | (2006.01) | |
| *C07C 49/84* | (2006.01) | |
| *C07C 69/92* | (2006.01) | |
| *C09K 19/04* | (2006.01) | |
| *C09K 19/52* | (2006.01) | |

(52) U.S. Cl.
CPC ............ *C07D 321/10* (2013.01); *C07C 49/84* (2013.01); *C07C 69/92* (2013.01); *C09K 19/04* (2013.01); *C09K 2019/0448* (2013.01); *C09K 19/52* (2013.01); *C09K 2219/03* (2013.01)

(58) Field of Classification Search
CPC ...... C07D 321/10; C09K 19/04; C09K 19/52; C09K 2019/0448; C09K 2219/03; C07C 49/84; C07C 69/92
See application file for complete search history.

(56) References Cited

U.S. PATENT DOCUMENTS

| | | | |
|---|---|---|---|
| 2003/0006398 A1 | 1/2003 | Yumoto et al. | |
| 2014/0160420 A1* | 6/2014 | Wang .................. | G02F 1/13718 349/176 |
| 2020/0071615 A1 | 3/2020 | Kodama et al. | |

FOREIGN PATENT DOCUMENTS

| | | |
|---|---|---|
| JP | 2002-179670 A | 6/2002 |
| JP | 2002-302487 A | 10/2002 |
| JP | 2003-55315 A | 2/2003 |
| WO | WO 2018/194157 A1 | 10/2018 |

OTHER PUBLICATIONS

International Preliminary Report on Patentability and Written Opinion of the International Searching Authority (PCT/IB/326, PCT/IB/373, and PCT/ISA/237) for International Application No. PCT/JP2019/031630, dated Mar. 18, 2021, with English translation of the Written Opinion.
International Search Report (Form PCT/ISA/210) for International Application No. PCT/JP2019/031630, dated Oct. 15, 2019, with English translation.
Kicková et al., "Synthesis and properties of macrocyclic diazene switch with binaphthalene unit attached acrylamide linkers," Chemical Papers, vol. 67, No. 1, 2013, pp. 101-109.
Office Action dated Apr. 12, 2022 for Japanese Patent Application No. 2020-541091, with English translation.

* cited by examiner

*Primary Examiner* — Timothy R Rozof

(74) *Attorney, Agent, or Firm* — Birch, Stewart, Kolasch & Birch, LLP

(57) ABSTRACT

The present invention provides a compound having an excellent rate of change in HTP due to exposure. The present invention further provides a composition formed of the compound, a cured product, an optically anisotropic body, and a reflective film.

The compound of the present invention is a compound represented by General Formula (1).

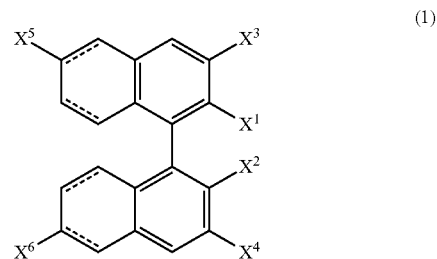

(1)

12 Claims, No Drawings

COMPOUND, COMPOSITION, CURED PRODUCT, OPTICALLY ANISOTROPIC BODY, AND REFLECTIVE FILM

CROSS-REFERENCE TO RELATED APPLICATIONS

This application is a Continuation of PCT International Application No. PCT/JP2019/031630 filed on Aug. 9, 2019, which claims priority under 35 U.S.C. § 119(a) to Japanese Patent Application No. 2018-167217 filed on Sep. 6, 2018. The above application is hereby expressly incorporated by reference, in its entirety, into the present application.

BACKGROUND OF THE INVENTION

1. Field of the Invention

The present invention relates to a compound, a composition, a cured product, an optically anisotropic body, and a reflective film.

2. Description of the Related Art

A compound exhibiting liquid crystallinity (hereinafter, also referred to as a "liquid crystalline compound") can be applied to various uses. For example, the liquid crystalline compound is applied to manufacture of an optically anisotropic body typified by a retardation film, or to manufacture of a reflective film obtained by immobilizing a cholesteric liquid crystalline phase.

Generally, the cholesteric liquid crystalline phase is formed by adding a chiral compound to a nematic liquid crystal. Anna Kickova et al. Chemical Papers, 2013, vol. 67, pp. 101 to 109 discloses a chiral compound having a helical twisting power (HTP) to a liquid crystalline compound.

SUMMARY OF THE INVENTION

On the other hand, in recent years, there is a demand for a chiral compound which can arbitrarily change HTP by performing a certain treatment. For example, a chiral compound which greatly changes the intensity of HTP by exposure has been desired.

As a result of studies on the chiral compound disclosed in Anna Kickova et al. Chemical Papers, 2013, vol. 67, pp. 101 to 109, the present inventors have found that, in the chiral compound disclosed in Anna Kickova et al. Chemical Papers, 2013, vol. 67, pp. 101 to 109, the degree of change in intensity of HTP (hereinafter, also referred to as a "rate of change in HTP) does not reach the level currently desired.

Therefore, an object of the present invention is to provide a compound having an excellent rate of change in HTP due to exposure.

Another object of the present invention is to provide a composition formed of the compound, a cured product, an optically anisotropic body, and a reflective film.

As a result of intensive studies to achieve the above-described objects, the present inventors have found that the above-described objects can be achieved by a compound represented by General Formula (1) described later, and have completed the present invention.

That is, the present inventors have found that the above-described object can be achieved by the following configuration.

[1] A compound represented by General Formula (1) described later.
[2] The compound according to [1],
in which $A^1$ represents an aromatic hydrocarbon ring group or an aromatic heterocyclic group.
[3] The compound according to [1] or [2],
in which $X^1$ and $X^2$ are bonded to each other to form a ring.
[4] The compound according to any one of [1] to [3],
in which at least one of $X^1$, $X^3$, or $X^5$ represents the group represented by General Formula (2) described later, and
at least one of $X^2$, $X^4$, or $X^6$ represents the group represented by General Formula (2).
[5] The compound according to any one of [1], [2], or [4],
in which at least one of $X^3$, $X^4$, $X^5$, or $X^6$ represents the group represented by General Formula (2), and
at least one of $X^1$ or $X^2$ represents a group represented General Formula (A) described later.
[6] The compound according to any one of [1] to [5],
in which the group represented by General Formula (2) is a group represented by General Formula (3) described later,
[7] A composition comprising:
the compound according to any one of [1] to [6].
[8] The composition according to [7], further comprising:
a liquid crystalline compound.
[9] The composition according to [8],
in which the liquid crystalline compound has two polymerizable groups.
[10] A cured product obtained by curing the composition according to any one of [7] to [9].
[11] An optically anisotropic body obtained by curing the composition according to [8] or [9].
[12] A reflective film obtained by curing the composition according to [8] or [9].

According to the present invention, it is possible to provide a compound having an excellent rate of change in HTP due to exposure.

In addition, according to the present invention, it is possible to provide a composition formed of the compound, a cured product, an optically anisotropic body, and a reflective film.

DESCRIPTION OF THE PREFERRED EMBODIMENTS

Hereinafter, the present invention will be described in detail.

The description of the constitutional requirements described below is made on the basis of representative embodiments of the present invention, but it should not be construed that the present invention is limited to those embodiments.

In the present specification, a numerical range represented using "to" means a range including numerical values described before and after the preposition "to" as a lower limit value and an upper limit value.

In addition, in the present specification, "(meth)acryloyloxy group" is a notation representing both an acryloyloxy group and a methacryloyloxy group.

In a notation for a group (atomic group) in the present specification, in a case where the group is denoted without specifying whether it is substituted or unsubstituted, the group includes both a group having no substituent and a group having a substituent. For example, "alkyl group" denotes not only an alkyl group having no substituent (unsubstituted alkyl group) but also an alkyl group having a substituent (substituted alkyl group).

In the present specification, in a case of simply referring to a substituent, examples of the substituent include the following substituent T.

(Substituent T)

Examples of the substituent T include a halogen atom (a fluorine atom, a chlorine atom, a bromine atom, an iodine atom, and the like), an alkyl group, a cycloalkyl group, an alkenyl group, a cycloalkenyl group, an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an amino group (including an alkylamino group and an anilino group), an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclic thio group, a sulfamoyl group, a sulfo group, an alkyl or arylsulfinyl group, an alkyl or arylsulfonyl group, an acyl group, an aryloxycarbonyl group, an alkoxycarbonyl group, a carbamoyl group, an aryl or heterocyclic azo group, an imido group, a phosphino group, a phosphinyl group, a phosphinyloxy group, a phosphinylamino group, and a silyl group.

Among the above-described substituents, a substituent having a hydrogen atom may be further substituted with any of the above-described substituents in the portion of the hydrogen atom in the substituent.

The bonding direction of a divalent group denoted in the present specification is not limited unless otherwise specified. For example, in a compound represented by the general formula "L-M-N", in a case where M is —OCO—C(CN)=CH—, and the position bonded to the L side is defined as *1 and the position bonded to the N side is defined as *2, M may be *1-OCO—C(CN)=CH—*2 or *1-CH=C(CN)—COO—*2.

[Compound According to Embodiment of Present Invention]

A feature of a compound according to an embodiment of the present invention is that the compound has a structure in which fused rings are linked to each other, and a group represented by General Formula (2) is linked to the fused ring.

Hereinafter, the compound according to the embodiment of the present invention will be described.

The compound according to the embodiment of the present invention is a compound represented by General Formula (1).

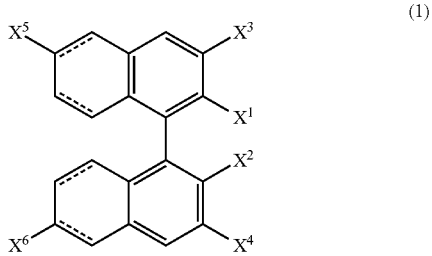

(1)

In General Formula (1), a portion where the solid line and the broken line are parallel to each other represents a single bond or a double bond. For example, in the compound represented by General Formula (1), in a case where the portion where the solid line and the broken line are parallel to each other is a single bond, the compound represented by General Formula (1) corresponds to a compound represented by General Formula (1-1), and in a case where the portion where the solid line and the broken line are parallel to each other is a double bond, the compound represented by General Formula (1) corresponds to a compound represented by General Formula (1-2).

Among these, a compound represented by General Formula (1-2) is preferable.

$X^1$ to $X^6$ in General Formula (1-1) and General Formula (1-2) respectively have the same meaning as $X^1$ to $X^6$ in General Formula (1).

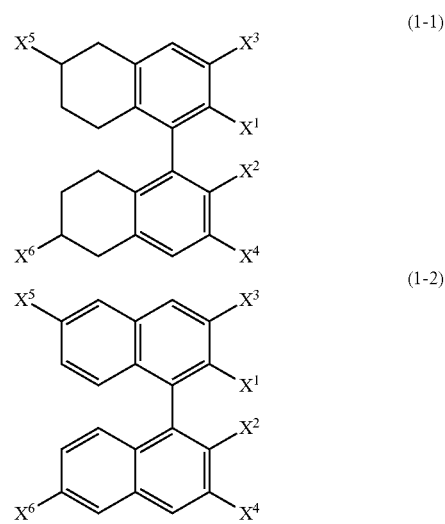

In General Formula (1), $X^1$ to $X^6$ each independently represent a hydrogen atom or a substituent. However, at least one of $X^1$, $X^2$, $X^3$, $X^4$, $X^5$, or $X^6$ represents a group represented by General Formula (2). $X^1$ and $X^2$ may be bonded to each other to form a ring.

$(R^1)_n$-$A^1$-$C^xO$—CH=CH—*     (2)

In General Formula (2), the positional relationship between the group represented by "$(R^1)_n$-$A^1$-$C^xO$—" and the bonding position represented by "-*" is not particularly limited, and the positional relationship may be trans type (the group represented by "$(R^1)_n$-$A^1$-$C^xO$—" and the bonding position represented by "-*" are arranged on the opposite side of the double bond) or cis type (the group represented by "$(R^1)_n$-$A^1$-$C^xO$—" and the bonding position represented by "-*" are arranged on the same side of the double bond).

In General Formula (2), $A^1$ represents a hydrocarbon ring group or a heterocyclic group, n represents an integer of 0 or more, $R^1$ represents a substituent, * represents a bonding position to the fused ring in General Formula (1), and a carbon atom $C^x$ is bonded to a carbon atom in $A^1$.

The number of groups represented by General Formula (2) in $X^1$ to $X^6$ is 1 to 6, preferably 2 or 4 and more preferably 2.

Among these, it is preferable that at least one of $X^1$, $X^3$, or $X^5$ is the group represented by General Formula (2) and at least one of $X^2$, $X^4$, or $X^6$ represents the group represented by General Formula (2), and it is more preferable that one of $X^1$, $X^3$, or $X^5$ is the group represented by General Formula (2) and one of $X^2$, $X^4$, or $X^6$ is the group represented by General Formula (2).

For example, in at least one combination selected from the group consisting of a combination of $X^1$ and $X^2$, a combination of $X^3$ and $X^4$, and a combination of $X^5$ and $X^6$, it is preferable that at least one constituent is the group represented by General Formula (2), and it is more preferable that both are the group represented by General Formula (2).

Hereinafter, the group represented by General Formula (2) will be described in detail.

In General Formula (2), n represents an integer of 0 or more. Among these, n is preferably an integer of 0 to 2, more preferably 0 or 1, and still more preferably 1.

In General Formula (2), $A^1$ represents a hydrocarbon ring group or a heterocyclic group.

Examples of the hydrocarbon ring group include an aliphatic hydrocarbon ring group and an aromatic hydrocarbon ring group. The number of ring members of a hydrocarbon ring constituting the hydrocarbon ring group is not particularly limited, but is preferably 5 to 10.

The aliphatic hydrocarbon ring constituting the aliphatic hydrocarbon ring group may have a monocyclic structure or a polycyclic structure. In a case where the aliphatic hydrocarbon ring has a polycyclic structure, it is preferable that at least one of the rings included in the polycyclic structure is a 5- or more membered ring.

The number of carbon atoms in the above-described aliphatic hydrocarbon ring is not particularly limited, but is preferably 5 to 12, more preferably 5 to 10, and still more preferably 5 or 6. Specific examples of the aliphatic hydrocarbon ring include a cyclopentane ring, a cyclohexane ring, a cycloheptane ring, a cyclooctane ring, a norbornene ring, and an adamantane ring. Among these, a cyclopentane ring or a cyclohexane ring is preferable.

The aromatic hydrocarbon ring constituting the aromatic hydrocarbon ring group may have a monocyclic structure or a polycyclic structure. In a case where the aromatic hydrocarbon ring has a polycyclic structure, it is preferable that at least one of the rings included in the polycyclic structure is a 5- or more membered ring.

The number of carbon atoms in the above-described aromatic hydrocarbon ring is not particularly limited, but is preferably 6 to 18 and more preferably 6 to 10. Specific examples of the aromatic hydrocarbon ring include a benzene ring, a naphthalene ring, an anthracene ring, a phenanthrene ring, and a fluorene ring. Among these, a benzene ring or a naphthalene ring is preferable, and a benzene ring is more preferable.

Examples of the heterocyclic group include an aliphatic heterocyclic group and an aromatic heterocyclic group. The number of ring members of a hetero ring constituting the heterocyclic group is not particularly limited, but is usually 5 to 10.

The aliphatic hetero ring constituting the aliphatic heterocyclic group may have a monocyclic structure or a polycyclic structure. In a case where the aliphatic hetero ring has a polycyclic structure, it is preferable that at least one of the rings included in the polycyclic structure is a 5- or more membered ring.

Examples of a hetero atom included in the above-described aliphatic hetero ring include a nitrogen atom, an oxygen atom, and a sulfur atom. The number of ring members in the above-described aliphatic hetero ring is not particularly limited, but is preferably 5 to 10. Specific examples of the above-described aliphatic hetero ring include an oxolane ring, an oxane ring, a piperidine ring, and a piperazine ring. In the aliphatic hetero ring, $—CH_2—$ constituting the ring may be replaced with $—CO—$, and examples thereof include a phthalimide ring.

The aromatic hetero ring constituting the aromatic heterocyclic group may have a monocyclic structure or a polycyclic structure. In a case where the aromatic hetero ring has a polycyclic structure, it is preferable that at least one of the rings included in the polycyclic structure is a 5- or more membered ring.

Examples of a hetero atom included in the above-described aromatic heterocyclic group include a nitrogen atom, an oxygen atom, and a sulfur atom. The number of ring members in the above-described aromatic hetero ring is not particularly limited, but is preferably 5 to 18. Specific examples of the above-described aromatic hetero ring include a pyridine ring, a pyridazine ring, a pyrimidine ring, a pyrazine ring, a triazine ring, a thiophene ring, a thiazole ring, and an imidazole ring.

By removing (n+1) hydrogen atoms corresponding to the number n of substituents represented by $R^1$ from the hydrocarbon ring or hetero ring described above, the hydrocarbon ring group or heterocyclic group represented by $A^1$ is obtained.

In General Formula (2), as $A^1$, the aromatic hydrocarbon ring group or the aromatic heterocyclic group is preferable, a benzene ring group or a naphthalene ring group is more preferable, and a benzene ring group is still more preferable. In the compound according to the embodiment of the present invention, in a case where $A^1$ is the aromatic hydrocarbon ring group or the aromatic heterocyclic group, the conjugated system including the fused ring is longer, so that the absorption efficiency of long wavelength light (particularly light having a wavelength of 365 nm) is improved and photoisomerization in a case of being exposed easily occurs.

In General Formula (2), $R^1$ represents a substituent. In a case where n is 2 or more, a plurality of $R^1$'s may be the same or different from each other.

Examples of the substituent represented by $R^1$ include a halogen atom, a hydroxyl group, an alkoxy group, an alkyl group, an acyloxy group, an alkoxycarbonyl group, a phenoxycarbonyl group, a hydrocarbon ring group, a heterocyclic group, and a group of a combination of these groups.

In addition, the definitions of hydrocarbon ring group and heterocyclic group as the substituent represented by $R^1$ are the same as the definitions of hydrocarbon ring group and heterocyclic group described in $A^1$.

The substituent represented by $R^1$ in General Formula (2) may be further substituted with a substituent. For example, the substituent represented by $R^1$ may be further substituted with a polymerizable group. The polymerizable group is not particularly limited as long as it is a known polymerizable group, and examples thereof include a (meth)acryloyloxy group, a vinyl group, a maleimide group, an acetyl group, a styryl group, an allyl group, an epoxy group, an oxetane group, and a group including these groups.

In General Formula (2), in a case where $A^1$ is a benzene ring group and n is 1 or more, it is preferable that $R^1$ is bonded to the carbonyl group in General Formula (2) at the para position. In a case where $A^1$ is a naphthalene ring group, it is preferable that the carbon atom $C^x$ in General Formula (2) is bonded at the 2-position and $R^1$ is bonded at the 5- to 7-position.

From the viewpoint that HTP of the compound before changing HTP due to exposure or the like (hereinafter, also referred to as an "initial HTP") is more excellent, the group represented by General Formula (2) is preferably a group represented by General Formula (3).

$$R^2\text{-}(A^3\text{-}Z^1)_m\text{-}A^2\text{-}C^xO—CH=CH—* \tag{3}$$

In General Formula (3), the positional relationship between the group represented by "$R^2\text{-}(A^3\text{-}Z^1)_m\text{-}A^2\text{-}C^xO\text{—}$" and the bonding position represented by "-*" is not particularly limited, and the positional relationship may be trans type (the group represented by "$R^2\text{-}(A^3\text{-}Z^1)_m\text{-}A^2\text{-}C^xO\text{—}$" and the bonding position represented by "-*" are arranged on the opposite side of the double bond) or cis type (the group represented by "$R^2\text{-}(A^3\text{-}Z^1)_m\text{-}A^2\text{-}C^xO\text{—}$" and the bonding position represented by "-*" are arranged on the same side of the double bond).

In General Formula (3), m represents an integer of 1 or 2, and is preferably 1.

In General Formula (3), * represents a bonding position to the fused ring in General Formula (1).

In General Formula (3), a carbon atom $C^x$ is bonded to a carbon atom in $A^2$.

In General Formula (3), $R^2$ represents a hydrogen atom or a substituent.

Examples of the substituent represented by $R^2$ include a halogen atom, a hydroxyl group, an alkoxy group, and an alkyl group. Among these, a hydroxyl group or an alkoxy group is preferable.

In General Formula (3), $Z^1$ represents a single bond, —O—, —S—, —CH$_2$O—, —CO—, —COO—, —CO—S—, —O—CO—O—, —CO—NH—, —CH$_2$S—, —CF$_2$O—, —CF$_2$S—, —CH═CH—COO—, —CH═CH—OCO—, —OCO—C(CN)═CH—, —COO—CH$_2$CH$_2$—, —OCO—CH$_2$CH$_2$—, —COO—CH$_2$—, —OCO—CH$_2$—, —CH═CH—, —N═N—, —CH═N—N═CH—, —CF═CF—, or —C≡C—.

In a case of a plurality of $Z^1$'s, the plurality of $Z^1$'s may be the same or different from each other.

Among these, $Z^1$ is preferably a single bond, —COO—, or —CH═CH—COO—.

In General Formula (3), $A^2$ and $A^3$ each independently represent a hydrocarbon ring group or a heterocyclic group. Among these, as $A^2$ and $A^3$, an aromatic hydrocarbon ring group is preferable, and a phenylene group is more preferable.

In addition, the definitions of hydrocarbon ring group and heterocyclic group represented by $A^2$ and $A^3$ of General Formula (3) are the same as the definitions of hydrocarbon ring group and heterocyclic group described in $A^1$ of General Formula (2). However, the hydrocarbon ring group and heterocyclic group represented by $A^2$ and $A^3$ have a structure in which two hydrogen atoms are removed from the hydrocarbon ring and the hetero ring.

In a case where m is 2, a plurality of $Z^1$'s and $A^3$'s may be respectively the same or different from each other.

The compound represented by General Formula (1) may have, as $X^1$ to $X^6$, a substituent other than the group represented by General Formula (2) or General Formula (3).

The substituent other than the group represented by General Formula (2) or General Formula (3) is not particularly limited, and examples thereof include a halogen atom, a hydroxyl group, —CHO, an alkoxy group, an alkyl group, and a group represented by General Formula (A). Among these, a hydroxyl group, —CHO, an alkoxy group, or a group represented by General Formula (A) is preferable, and an alkoxy group or a group represented by General Formula (A) is more preferable.

$$R^3\text{-}(A^4\text{-}Z^2)_k\text{—}* \quad (A)$$

In General Formula (A), k represents an integer of 1 or more, and is preferably an integer of 1 to 5 and more preferably an integer of 1 to 3.

In General Formula (A), * represents a bonding position to the fused ring in General Formula (1).

In General Formula (A), $R^3$ represents a hydrogen atom or a substituent.

Examples of the substituent represented by $R^3$ include a halogen atom, a hydroxyl group, an alkoxy group, and an alkyl group. Among these, an alkoxy group is preferable.

In General Formula (A), $Z^2$ represents a single bond, —O—, —S—, —CH$_2$O—, —CO—, —COO—, —CO—S—, —O—CO—O—, —CO—NH—, —CH$_2$S—, —CF$_2$O—, —CF$_2$S—, —CH═CH—COO—, —CH═CH—OCO—, —OCO—C(CN)═CH—, —COO—CH$_2$CH$_2$—, —OCO—CH$_2$CH$_2$—, —COO—CH$_2$—, —OCO—CH$_2$—, —CH═CH—, —N═N—, —CH═N—N═CH—, —CF═CF—, or —C≡C—.

Among these, $Z^2$ is preferably a single bond, —COO—, —CH═CH—COO—, or —OCO—C(CN)═CH—.

In General Formula (A), $A^4$ represents a hydrocarbon ring group or a heterocyclic group. Among these, as $A^4$, an aromatic hydrocarbon ring group is preferable, and a phenylene group is more preferable.

In addition, the definitions of hydrocarbon ring group and heterocyclic group represented by $A^4$ of General Formula (A) are the same as the definitions of hydrocarbon ring group and heterocyclic group described in $A^1$ of General Formula (2). However, the hydrocarbon ring group and heterocyclic group represented by $A^4$ have a structure in which two hydrogen atoms are removed from the hydrocarbon ring and the hetero ring.

In a case where k is 2 or more, a plurality of $Z^2$'s and $A^4$'s may be respectively the same or different from each other.

In General Formula (1), a plurality of groups selected from $X^1$ to $X^6$ may be bonded to each other to form a ring. For example, it is preferable that two groups selected from $X^1$ to $X^6$ are bonded to each other to form a ring. In this case, a plurality of combinations of the above-described two groups of $X^1$ to $X^6$ may exist. For example, $X^1$ and $X^3$ may be bonded to each other to form a ring, and at the same time, $X^2$ and $X^4$ may be bonded to each other to form a ring.

Among these, as the combination of two groups selected from $X^1$ to $X^6$, any one of a combination of $X^1$ and $X^3$, $X^1$ and $X^2$, or $X^2$ and $X^4$ is preferable, and from the viewpoint that the initial HTP is excellent, it is preferable that $X^1$ and $X^2$ are bonded to each other to form a ring.

The group formed by bonding two groups of a combination selected from $X^1$ to $X^6$ to each other is not particularly limited, and examples thereof include a single bond or a divalent linking group.

Examples of the divalent linking group include —O—, —CO—, —COO—, —CO—S—, —SO$_2$—, —NR— (R represents a hydrogen atom or an alkyl group), a divalent hydrocarbon group (for example, an alkylene group, an alkenylene group (for example, —CH═CH—), an alkynylene group (for example, —C≡C—), and an arylene group), and a group of a combination of these groups.

Among these, it is preferable that $X^1$ and $X^2$ are bonded to each other to form "—O-alkylene group (preferably having 1 to 3 carbon atoms)-O—" or "—OCO-arylene group (preferably, phenylene group)-COO—", and it is more preferable to form "—O-alkylene group (preferably having 1 to 3 carbon atoms)-O—".

In General Formula (1), in a case where at least one of $X^3$, $X^4$, $X^5$, or $X^6$ is the group represented by General Formula (2) and $X^1$ and $X^2$ are not bonded to each other to form a ring, it is preferable that at least one of $X^1$ or $X^2$ is a hydroxyl group, an alkoxy group, or the group represented by General Formula (A) described above.

Among these, from the viewpoint that the overall structure of the compound is longer and the initial HTP is further improved, it is more preferable that at least one of $X^3$, $X^4$, $X^5$, or $X^6$ is the group represented by General Formula (2) (preferably, at least one of $X^5$ or $X^6$ is the group represented by General Formula (2)), and at least one of $X^1$ or $X^2$ is the group represented by General Formula (A) described above, in which k in General Formula (A) is 2 or more.

In a case where $X^1$ and $X^2$ are the group represented by General Formula (A), k preferably represents an integer of 2 to 5, and more preferably represents 2 or 3.

In addition, $R^3$, $Z^2$ which may exist plurally, and $A^4$ which may exist plurally in a case where $X^1$ and $X^2$ are the group represented by General Formula (A) are as described above.

However, as $R^3$, a hydroxyl group or an alkoxy group is preferable, and an alkoxy group having 1 to 3 carbon atoms is more preferable.

In addition, as $Z^2$, —COO— or —OCO—C(CN)=CH— is preferable.

In addition, as $A^4$, an aromatic hydrocarbon ring group is preferable, and a phenylene group is more preferable.

The compound according to the embodiment of the present invention can be synthesized by a known method.

The compound according to the embodiment of the present invention may be an R-form or an S-form, or may be a mixture of R-form and S-form.

Specific examples of the compound according to the embodiment of the present invention are shown below.

CD-1

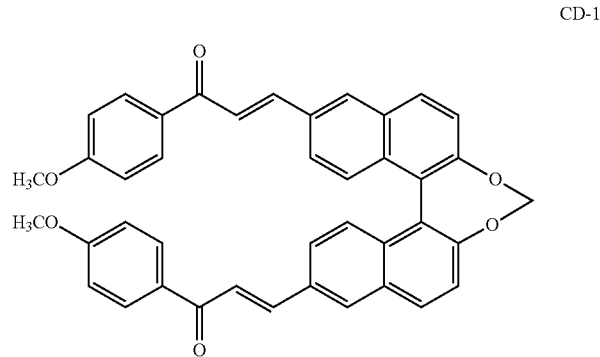

CD-2

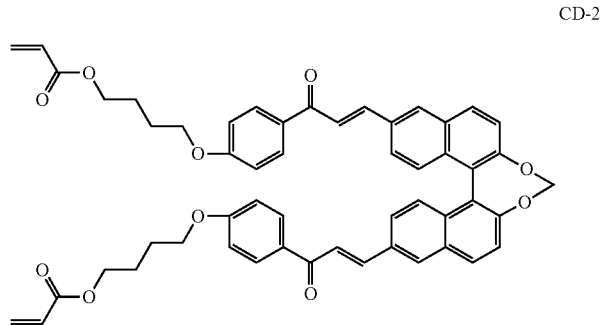

CD-3

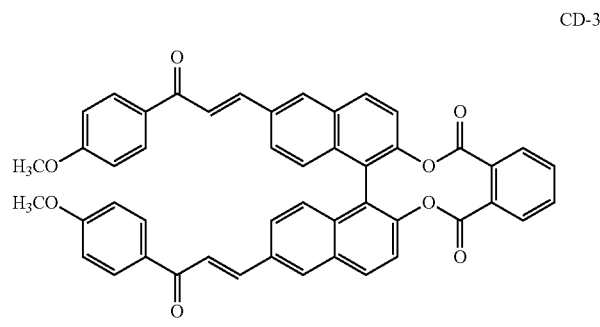

CD-4

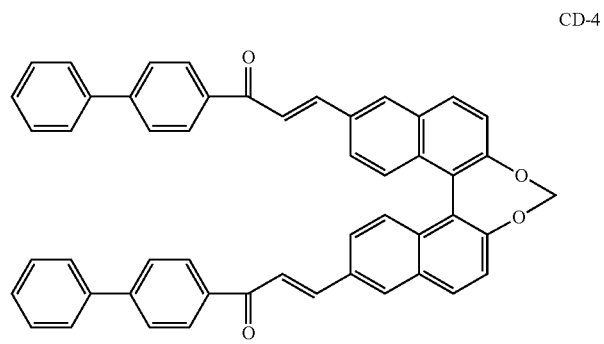

CD-5

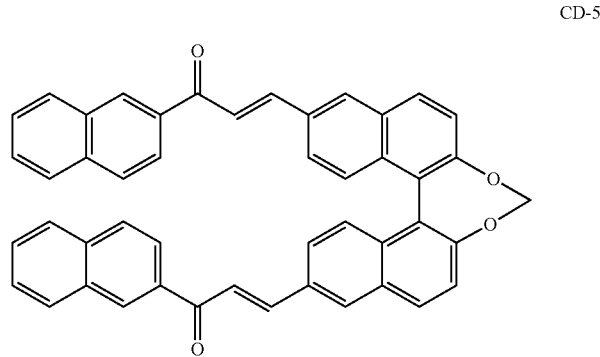

CD-6

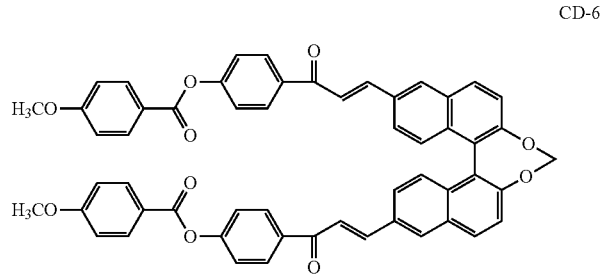

-continued
CD-7
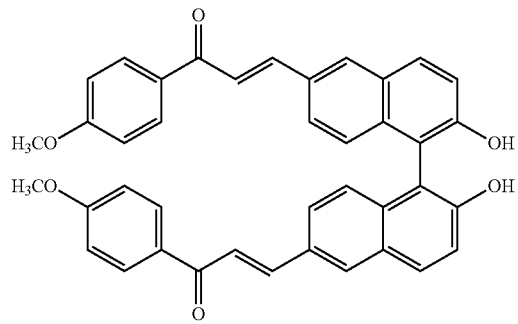
CD-8
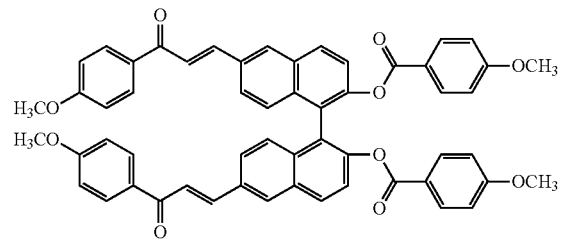
CD-9
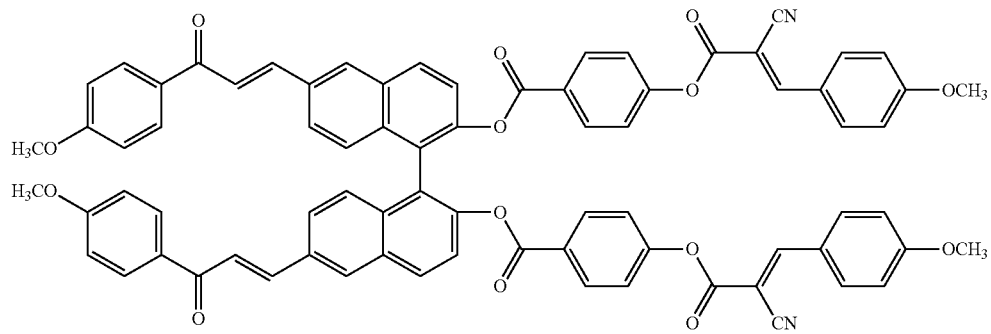
CD-10
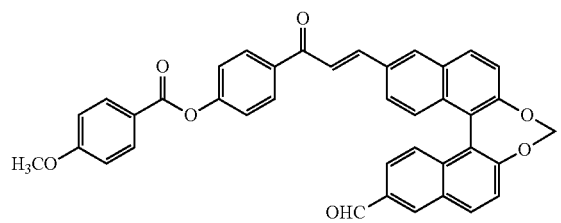
CD-11
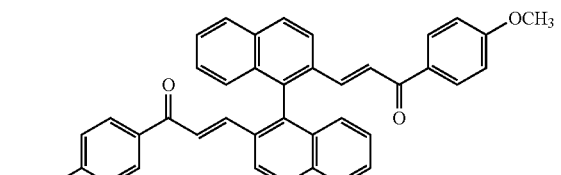
CD-12
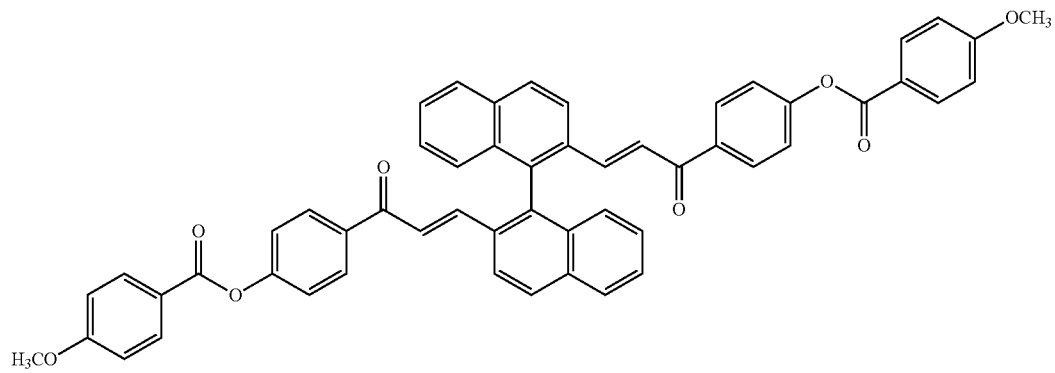
CD-13
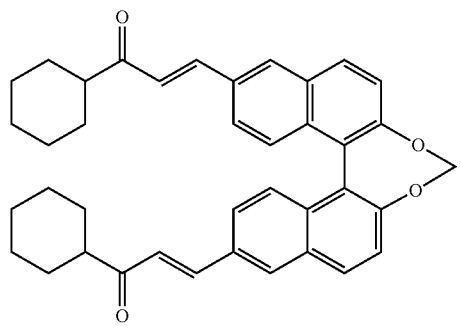
CD-14
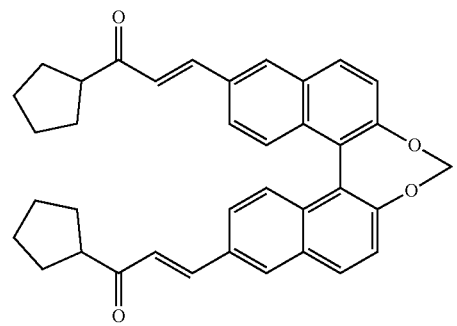

-continued
CD-15
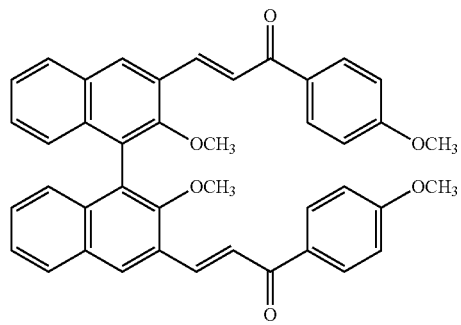
CD-16
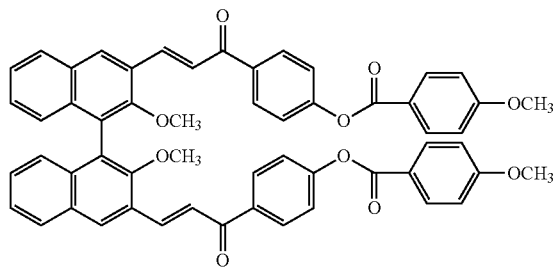
CD-17
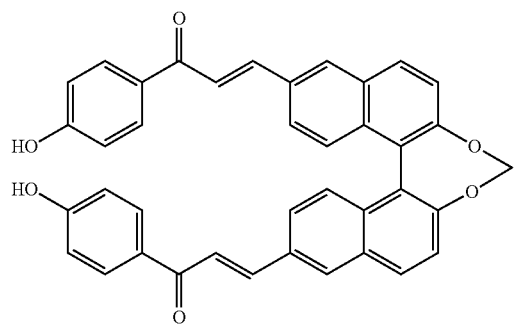
CD-18
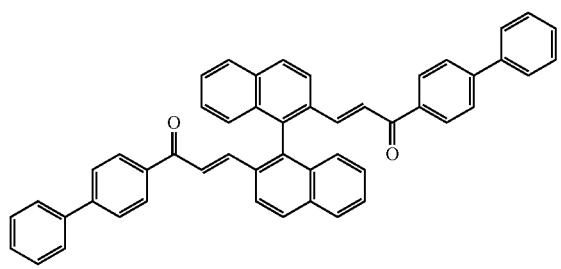
CD-19
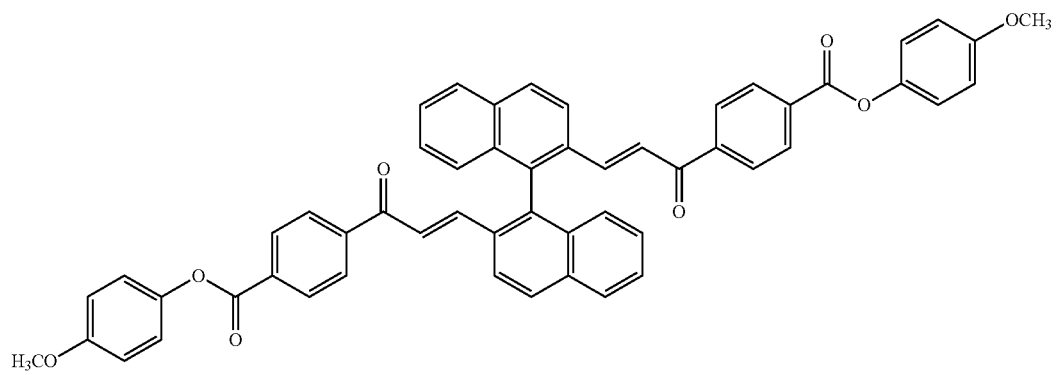
CD-20
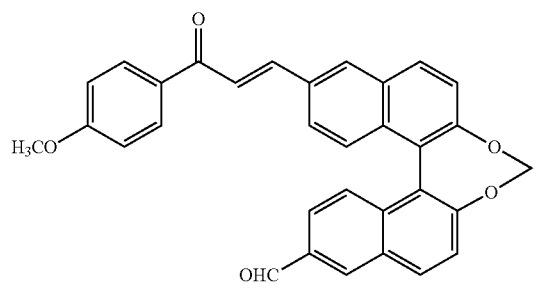
CD-21
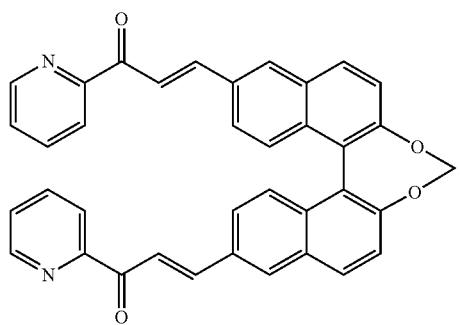

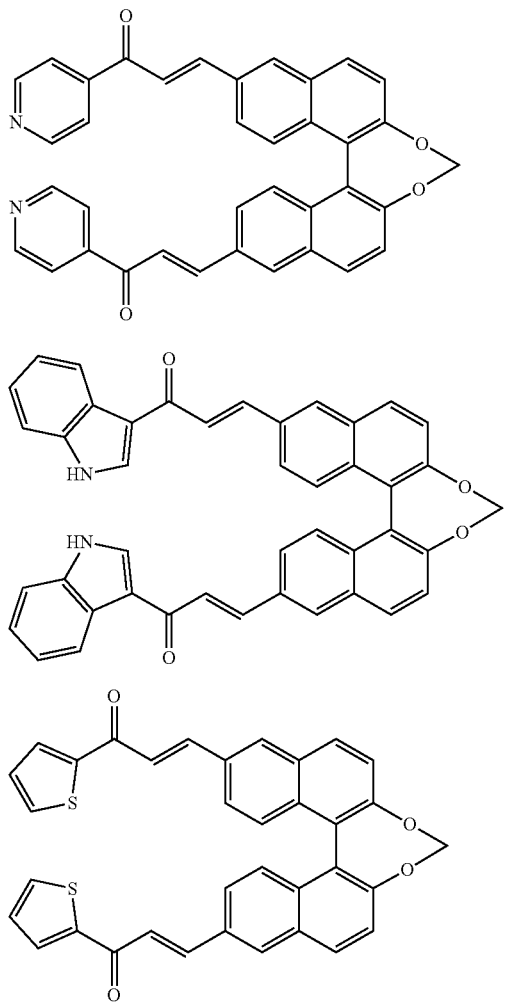
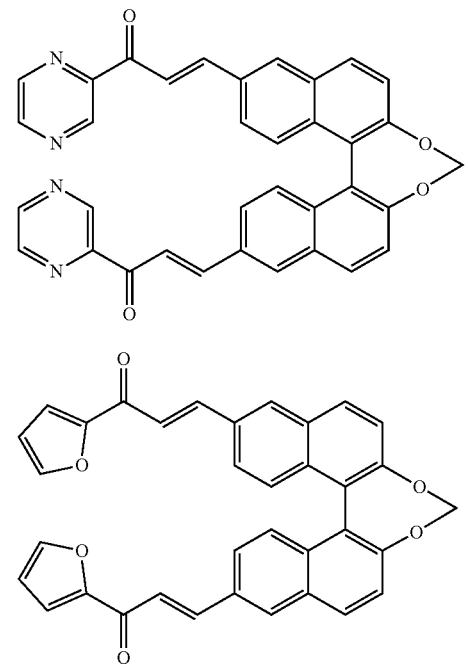

The compound according to the embodiment of the present invention can be applied to various uses and is suitably used as a so-called chiral compound. For example, by using a composition obtained by mixing the compound according to the embodiment of the present invention and a liquid crystalline compound, a cholesteric liquid crystalline phase can be formed.

Hereinafter, the composition will be described in detail.

[Composition]

Next, a composition according to an embodiment of the present invention will be described.

The composition according to an embodiment of the present invention is a composition including the compound according to the embodiment of the present invention.

It is preferably that the composition according to the embodiment of the present invention is a composition (liquid crystal composition) further including a liquid crystalline compound.

Hereinafter, each component included in the composition in a case where the composition according to the embodiment of the present invention is a liquid crystal composition will be described in detail.

<Compound According to Embodiment of Present Invention>

The composition according to the embodiment of the present invention includes the compound according to the embodiment of the present invention. The compound according to the embodiment of the present invention is as described above.

The content of the compound according to the embodiment of the present invention in the composition is not particularly limited, but is preferably 1% to 20% by mass, more preferably 2% to 15% by mass, and still more preferably 2% to 10% by mass with respect to the total mass of the liquid crystalline compound in the composition. The liquid crystalline compound will be described later.

In the composition, the compound according to the embodiment of the present invention may be used alone or in combination of two or more kinds thereof. In a case where two or more kinds thereof are used, it is preferable that the total content thereof is within the above-described range.

<Liquid Crystalline Compound>

In a case where the composition according to the embodiment of the present invention is a liquid crystal composition, the composition according to the embodiment of the present invention includes a liquid crystalline compound.

The liquid crystalline compound means a compound exhibiting liquid crystallinity, which is a compound other than the compound according to the embodiment of the present invention.

For the compound exhibiting liquid crystallinity, it is intended that the compound has properties of expressing a mesophase between a crystalline phase (low temperature side) and an isotropic phase (high temperature side) in a case of changing a temperature. As a specific observation method, optical anisotropy and fluidity derived from a liquid crystalline phase can be confirmed by performing an observation using a polarizing microscope while heating the compound or lowering a temperature of the compound with a hot stage system FP90, manufactured by METTLER TOLEDO, or the like.

The liquid crystalline compound is not particularly limited as long as it has liquid crystallinity, and examples thereof include a rod-like nematic liquid crystalline compound.

Examples of the rod-like nematic liquid crystalline compound include azomethines, azoxys, cyanobiphenyls, cyanophenyl esters, benzoic acid esters, cyclohexanecarboxylic acid phenyl esters, cyanophenylcyclohexanes, cyano-substituted phenylpyrimidines, alkoxy-substituted phenylpyrimidines, phenyldioxanes, tolans, and alkenylcyclohexylbenzonitriles. High-molecular-weight liquid crystalline compounds can also be used as well as low-molecular-weight liquid crystalline compounds.

The liquid crystalline compound may be polymerizable or non-polymerizable, but is preferably polymerizable.

From the viewpoint that the cholesteric liquid crystalline phase can be immobilized, as the liquid crystalline compound, a liquid crystalline compound having one or more polymerizable groups is preferable, a liquid crystalline compound having two or more polymerizable groups is more preferable, and a liquid crystalline compound having two polymerizable groups is still more preferable.

Rod-like liquid crystalline compounds having no polymerizable group are described in various documents (for example, Y. Goto et al., Mol. Cryst. Liq. Cryst. 1995, Vol. 260, pp. 23 to 28).

Meanwhile, a polymerizable rod-like liquid crystalline compound is obtained by introducing a polymerizable group into the rod-like liquid crystalline compound. Examples of the polymerizable group include an unsaturated polymerizable group, an epoxy group, and an aziridinyl group. Among these, an unsaturated polymerizable group is preferable and an ethylenically unsaturated polymerizable group is more preferable. The polymerizable group can be introduced into the molecule of the rod-like liquid crystalline compound by various methods. The number of polymerizable groups included in the polymerizable rod-like liquid crystalline compound is preferably 1 to 6, more preferably 1 to 3, and still more preferably 2. Two or more kinds of polymerizable rod-like liquid crystalline compounds may be used in combination. In a case of using two or more kinds of polymerizable rod-like liquid crystalline compounds in combination, the alignment temperature can be lowered.

As the liquid crystalline compound, a compound represented by General Formula (4) is preferable.

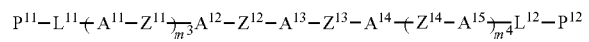

(4)

In General Formula (4), $P^{11}$ and $P^{12}$ each independently represent a hydrogen atom or a polymerizable group. However, at least one of $P^{11}$ or $P^{12}$ represents a polymerizable group. $L^{11}$ and $L^{12}$ each independently represent a single bond or a divalent linking group. $A^{11}$ to $A^{15}$ each independently represent an aromatic hydrocarbon ring group or aromatic heterocyclic group which may have a substituent. $Z^{11}$ to $Z^{14}$ each independently represent a single bond or a divalent linking group. $m^3$ and $m^4$ each independently represent an integer of 0 or 1.

In General Formula (4), the polymerizable group represented by $P^{11}$ and $P^{12}$ is not particularly limited, and suitable specific examples thereof include a polymerizable group represented by General Formulae (P-1) to (P-20). In the following formulae, * represents a bonding position to $L^{11}$ or $L^{12}$. In addition, Ra represents a hydrogen atom or a methyl group. In addition, Me represents a methyl group, and Et represents an ethyl group.

(P-1)

(P-2)

(P-3)

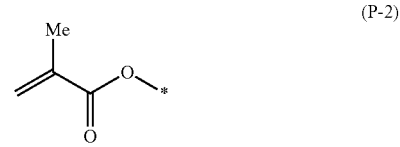

(P-4)

(P-5)

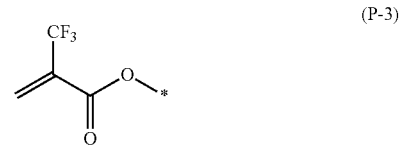

(P-6)

(P-7)

(P-8)

(P-9)

(P-10)

(P-11)

(P-12)

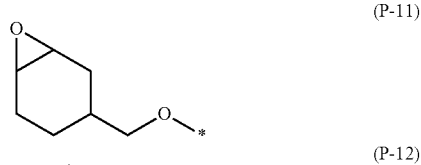

(P-13)

(P-14) 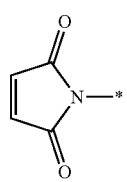

(P-15) 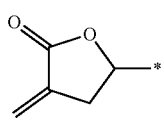

(P-16) 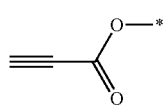

(P-17) 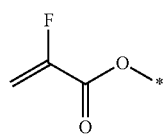

(P-18) 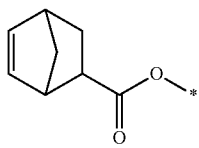

(P-19) 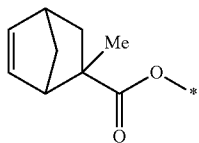

(P-20) 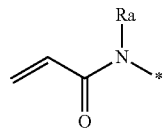

It is preferable that at least one of $P^{11}$ or $P^{12}$ represents a polymerizable group, and it is more preferable that any of $P^{11}$ and $P^{12}$ represent a polymerizable group.

In General Formula (4), the divalent linking group represented by $L^{11}$ and $L^{12}$ is not particularly limited, and examples thereof each independently include a linear or branched alkylene group having 1 to 20 carbon atoms, and a divalent linking group of a linear or branched alkylene group having 1 to 20 carbon atoms, in which one or more —$CH_2$— are replaced with one or more groups selected from the group consisting of —O—, —S—, —NH—, —N($CH_3$)—, —CO—, and —COO—.

As the divalent linking group represented by $L^{11}$ and $L^{12}$, a group of a linear or branched alkylene group having 1 to 20 carbon atoms, in which one or more —$CH_2$— are replaced with —O— is respectively preferable.

In General Formula (4), $A^{11}$ to $A^{15}$ each independently represent an aromatic hydrocarbon ring group which may have a substituent or an aromatic heterocyclic group which may have a substituent.

The definitions of aromatic hydrocarbon ring group and aromatic heterocyclic group are the same as the definitions of aromatic hydrocarbon ring group and aromatic heterocyclic group described in $A^1$ and $A^2$.

The above-described hydrocarbon ring group and heterocyclic group may or may not have a substituent. The number of substituents may be one or plural.

Among these, as the substituent, from the viewpoint that solubility of the compound represented by General Formula (4) is further improved, a fluorine atom, a chlorine atom, a fluoroalkyl group, an alkoxy group, or an alkyl group is preferable, and a fluoroalkyl group, an alkoxy group, or an alkyl group is more preferable.

The number of carbon atoms in the fluoroalkyl group and alkyl group, and the number of carbon atoms in an alkyl group of the alkoxy group are not particularly limited, but are preferably 1 to 10, more preferably 1 to 5, still more preferably 1 to 3, and particularly preferably 1.

The fluoroalkyl group is a group in which at least one hydrogen atom in the alkyl group is replaced with a fluorine atom, and it is preferable that all hydrogen atoms are replaced with fluorine atoms (so-called perfluoroalkyl group is preferable).

As $A^{11}$ to $A^{15}$, an aromatic hydrocarbon ring group which may have a substituent is preferable, and a phenylene group bonded at the 1-position and the 4-position is more preferable.

In General Formula (4), the divalent linking group represented by $Z^{11}$ to $Z^{14}$ is not particularly limited, and examples thereof include the above-described divalent linking group represented by $Z^1$ and $Z^2$ (groups other than a single bond among the groups described in $Z^1$ and $Z^2$). Among these, as $Z^{11}$ to $Z^{14}$, —COO— or —CH=CH— is preferable.

In general Formula (4), $m^3$ and $m^4$ each independently represent an integer of 0 or 1, preferably 0.

The compound represented by General Formula (4) can be synthesized by a known method.

Specific examples of the liquid crystalline compound are shown below.

LC-1

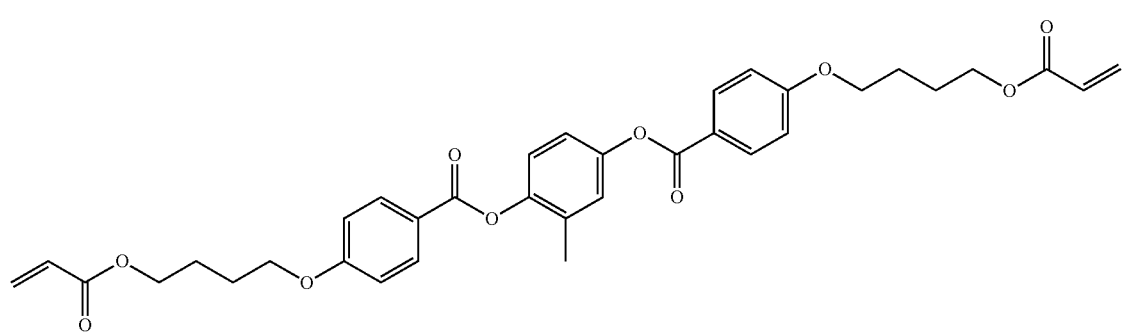

-continued
LC-2
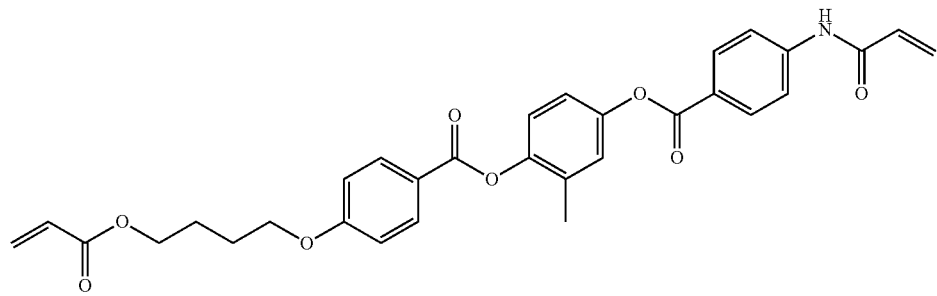
LC-3
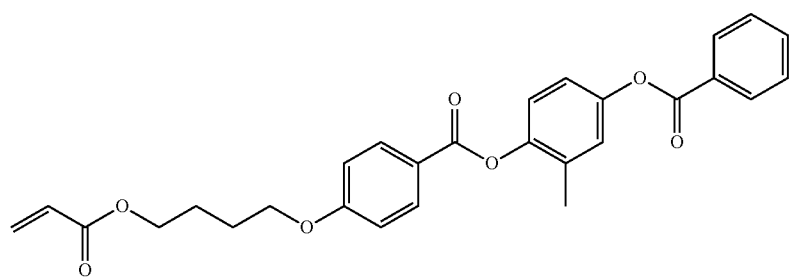
LC-4
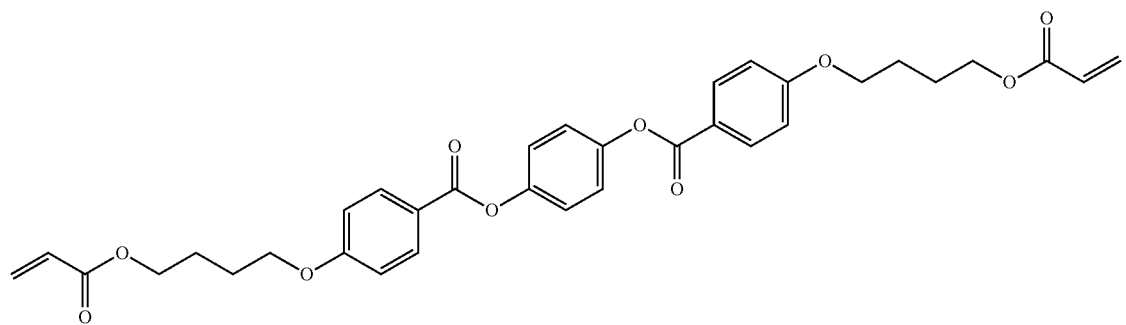
LC-5
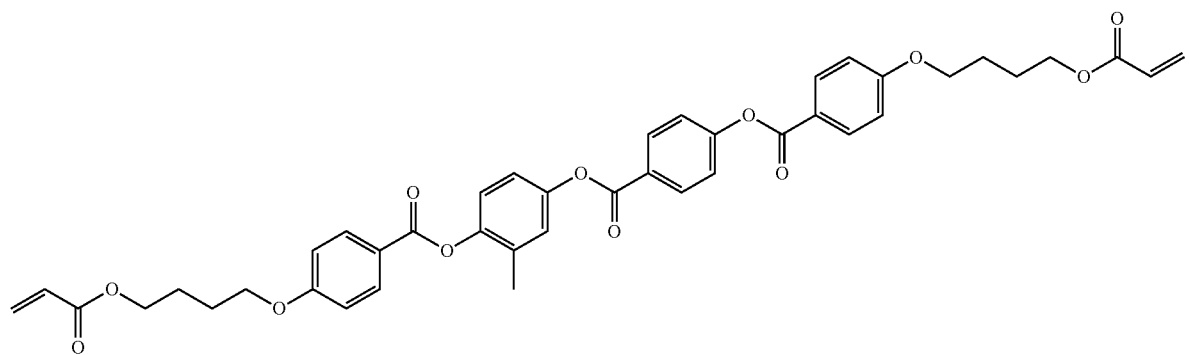

-continued
LC-6
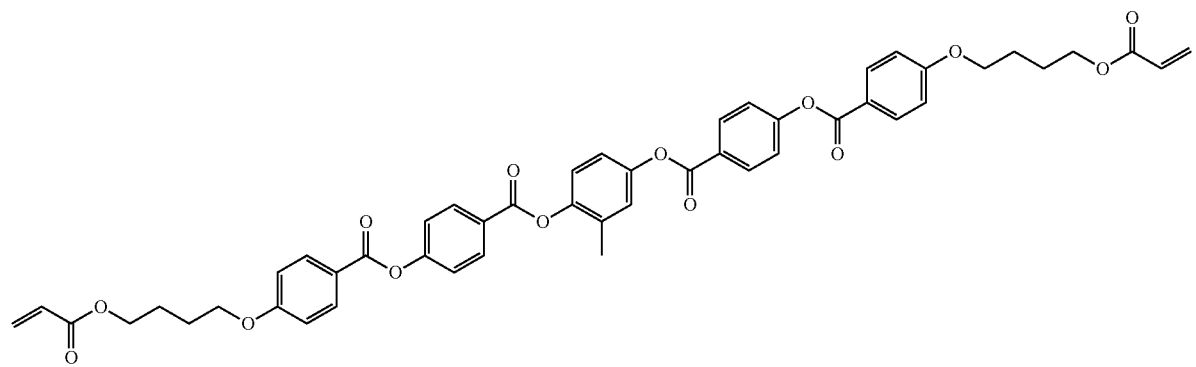
LC-7
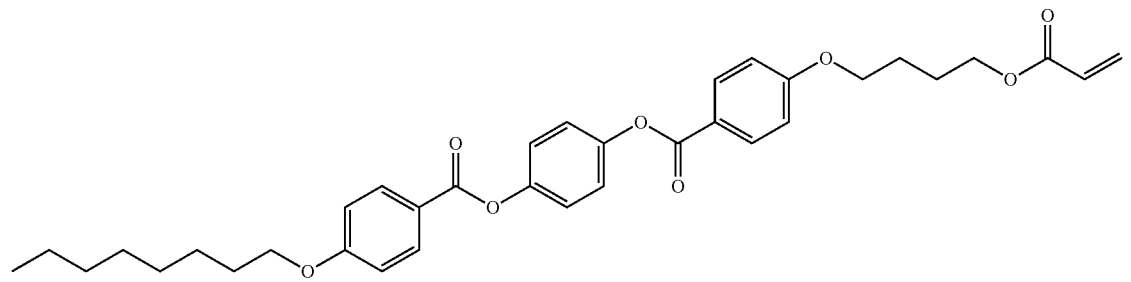
LC-8
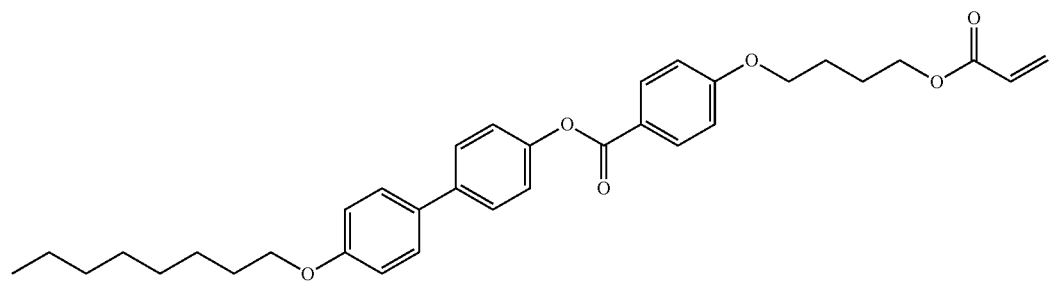
LC-9
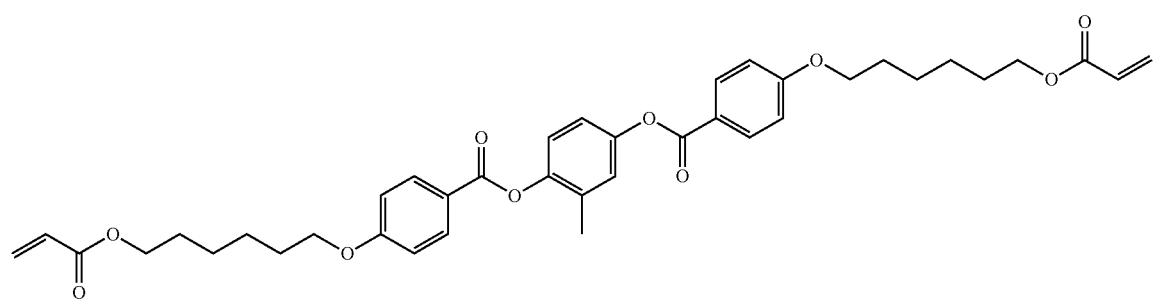
LC-10
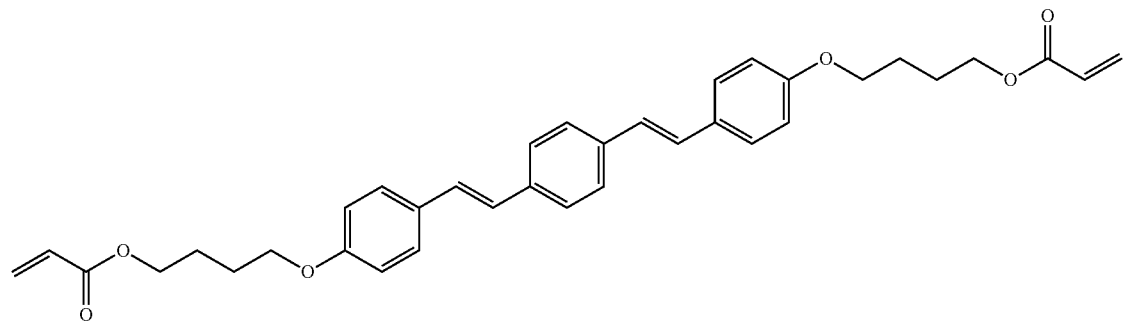

The content of the liquid crystalline compound in the composition is not particularly limited, but is preferably 5% to 99% by mass, more preferably 25% to 98% by mass, and still more preferably 75% to 98% by mass with respect to the total mass of solid contents of the composition.

The solid contents mean components other than a solvent in the composition. In a case where a component is not a solvent, the component is regarded as a solid content even in a case where the property of the component is liquid.

In the composition, the liquid crystalline compound may be used alone or in combination of two or more kinds thereof. In a case where two or more kinds thereof are used, it is preferable that the total content thereof is within the above-described range.

<Polymerization Initiator>

The composition may include a polymerization initiator.

Examples of the polymerization initiator include a photopolymerization initiator and a thermal polymerization initiator. Among these, a photopolymerization initiator capable of initiating a polymerization reaction by irradiation with ultraviolet rays is preferable. Examples of the photopolymerization initiator include an alkylphenone compound, an α-carbonyl compound, acyloin ether, an α-hydrocarbon-substituted aromatic acyloin compound, a polynuclear quinone compound, a phenazine compound, and an oxadiazole compound.

In a case where the composition includes a polymerization initiator, the content of the polymerization initiator in the composition is not particularly limited, but is preferably 0.1% to 20% by mass and more preferably 1% to 8% by mass with respect to the total mass of the liquid crystalline compound.

In the composition, the polymerization initiator may be used alone or in combination of two or more kinds thereof. In a case where two or more kinds thereof are used, it is preferable that the total content thereof is within the above-described range.

<Surfactant>

The composition may include a surfactant which contributes to a stable or rapid formation of liquid crystalline phase (for example, a nematic phase and a cholesteric phase).

Examples of the surfactant include a fluorine-containing (meth)acrylate-based polymer, compounds represented by General Formulae (X1) to (X3) described in WO2011/162291A, compounds represented by General Formula (I) described in paragraphs 0082 to 0090 of JP2014-119605A, and compounds described in paragraphs 0020 to 0031 of JP2013-047204A (JP5774518B). At an air interface of a layer, these compounds can reduce a tilt angle of molecules of a liquid crystalline compound or can cause a liquid crystalline compound to be substantially horizontally aligned.

In the present specification, "horizontally aligned" means that a molecular axis of the liquid crystalline compound (which corresponds to a long axis of the liquid crystalline compound in a case where the liquid crystalline compound is a rod-like liquid crystalline compound) is parallel to a surface of the layer of the composition (film surface), but the molecular axis is not required to be strictly parallel thereto. In the present specification, "horizontally aligned" means an alignment in which a tilt angle with the film surface is less than 20 degrees. In a case where the liquid crystalline compound is horizontally aligned near the air interface, alignment defects are less likely to occur, so that transparency in a visible light region is increased. On the other hand, in a case where molecules of the liquid crystalline compound are aligned at a large tilt angle with respect to the film surface, for example, in a case where a cholesteric phase is formed, a helical axis deviates from a normal line of the film surface. Therefore, reflectance may decrease or a fingerprint pattern may occur, so that haze may increase or diffractive may be exhibited, which is not preferable.

Examples of the fluorine-containing (meth) acrylate-based polymer which can be used as the surfactant also include polymers described in paragraphs 0018 to 0043 of JP2007-272185A.

In a case where the composition includes a surfactant, the content of the surfactant is not particularly limited, but is preferably 0.001% to 10% by mass and more preferably 0.05% to 3% by mass with respect to the total mass of the liquid crystalline compound.

In the composition, the surfactant may be used alone or in combination of two or more kinds thereof. In a case where two or more kinds thereof are used, it is preferable that the total content thereof is within the above-described range.

<Solvent>

The composition may include a solvent. As the solvent, a solvent which can dissolve each component of the composition is preferable. Examples thereof include methyl ethyl ketone, cyclohexanone, and a mixed solvent thereof.

In a case where the composition includes a solvent, the content of the solvent in the composition is preferably an amount at which the concentration of solid contents in the composition is 5% to 50% by mass, and more preferably an amount at which the concentration of solid contents in the composition is 10% to 40% by mass.

In the composition, the solvent may be used alone or in combination of two or more kinds thereof. In a case where two or more kinds thereof are used, it is preferable that the total content thereof is within the above-described range.

In addition to the above-described components, the composition may also include other additives such as an antioxidant, an ultraviolet absorber, a sensitizer, a stabilizer, a plasticizer, a chain transfer agent, a polymerization inhibitor, an anti-foaming agent, a leveling agent, a thickener, a flame retardant, a dispersant, a polymerizable monomer, and a coloring material such as a dye and a pigment.

[Cured Product]

The present invention also includes a cured product obtained by curing the above-described composition.

<Curing Method and Cured Product>

A method for curing (polymerizing and curing) the above-described composition is not particularly limited, and a known method can be adopted. Examples thereof include an aspect which includes a step X of bringing a predetermined substrate into contact with the composition to form a composition layer on the substrate, a step Y of exposing the composition layer, and a step Z of subjecting the composition layer to a curing treatment.

In particular, in a case where the composition is a liquid crystal composition including the liquid crystalline compound, according to this aspect, the liquid crystalline compound can be immobilized in an aligned state, and a so-called optically anisotropic body or a layer obtained by immobilizing a cholesteric liquid crystalline phase can be formed.

Hereinafter, the procedures of steps X to Z in a case of using the composition (liquid crystal composition) according to the embodiment of the present invention in an aspect of including the liquid crystalline compound will be described in detail.

The step X is a step of bringing a substrate into contact with the composition to form a composition layer on the substrate. The type of the substrate to be used is not particularly limited, and examples thereof include known substrates (for example, a resin substrate, a glass substrate, a ceramic substrate, a semiconductor substrate, and a metal substrate).

A method of bringing the substrate into contact with the composition is not particularly limited, and examples thereof include a method of applying the composition to the substrate and a method of immersing the substrate in the composition.

After bringing the substrate into contact with the composition, as necessary, a drying treatment may be performed in order to remove a solvent from the composition layer on the substrate. In addition, a heat treatment may be performed in order to promote the alignment of the liquid crystalline compound to be a liquid crystalline phase.

The step Y is a step of subjecting the composition layer to an exposure treatment using i-rays (wavelength: 365 nm) or the like.

In the compound according to the embodiment of the present invention, it is preferable that photoisomerization occurs due to the exposure treatment, so that HTP of the compound changes. In this exposure treatment, the degree of change in HTP can also be adjusted by appropriately adjusting the exposure amount, and/or the exposure wavelength and the like.

After the exposure, a heat treatment may be further performed in order to promote the alignment of the liquid crystalline compound to be a liquid crystalline phase.

The helical pitch (and thus the selective reflection wavelength and the like) of the liquid crystalline phase obtained here reflects HTP adjusted in the above-described exposure treatment.

The step Z is a step of subjecting the composition layer (preferably, composition layer in a state of liquid crystalline phase) undergone the step Y to a curing treatment.

A method of the curing treatment is not particularly limited, and examples thereof include a photo-curing treatment and a thermal-curing treatment. Among these, a photo-curing treatment is preferable.

In a case where a photo-curing treatment is performed as the curing treatment, it is preferable that the composition includes a photopolymerization initiator. The wavelength of the light irradiated in the photo-curing treatment is preferably different from the wavelength of the light used in the above-described exposure treatment, or it is preferable that the photopolymerization initiator is not sensitive to the wavelength of the light used in the exposure treatment.

The cured product obtained by the above-described treatments is preferably a layer obtained by immobilizing the liquid crystalline phase. In particular, in the cured product obtained by curing the composition according to the embodiment of the present invention, a layer obtained by immobilizing the cholesteric liquid crystalline phase is typically formed.

These layers do not need to exhibit liquid crystallinity anymore. More specifically, for example, as a state in which the cholesteric liquid crystalline phase is "immobilized," the most typical and preferred aspect is a state in which the alignment of the liquid crystalline compound, which is the cholesteric liquid crystalline phase, is retained. More specifically, the state is preferably a state in which the layer does not exhibit fluidity within a temperature range of usually 0° C. to 50° C., and under more severe conditions of a temperature range of −30° C. to 70° C., and in which the immobilized alignment morphology can be kept stable without being changed due to an external field or an external force.

[Optically Anisotropic Body and Reflective Film]

A cured product can be obtained by subjecting the composition to the curing treatment as described above.

The cured product obtained by curing the composition according to the embodiment of the present invention can be applied to various uses, and examples thereof include an optically anisotropic body and a reflective film. In other words, an optically anisotropic body or reflective film obtained by curing the above-described composition is mentioned as a suitable aspect.

The optically anisotropic body is intended to be a substance having optical anisotropy.

In addition, the reflective film corresponds to a layer obtained by immobilizing the above-described cholesteric liquid crystalline phase, and is a layer capable of reflecting light in a predetermined reflection band.

EXAMPLES

Hereinafter, the present invention will be described in more detail based on examples. The materials, the amounts of materials to be used, the proportions, the treatment details, the treatment procedure, or the like shown in the examples below may be modified appropriately as long as the modifications do not depart from the spirit of the present invention. Accordingly, the scope of the present invention should not be construed as being limited to the following examples.

[Synthesis of Compound]

<Synthesis of Compound CD-1>

A compound CD-1 was synthesized according to the following scheme.

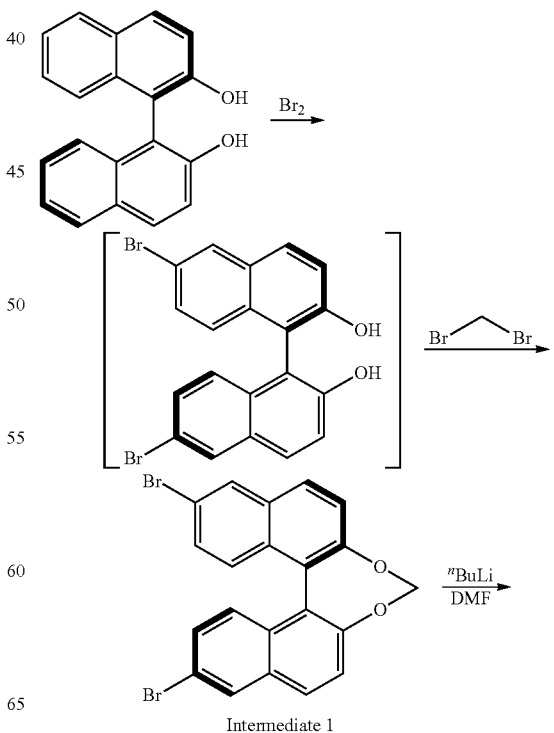

Intermediate 1

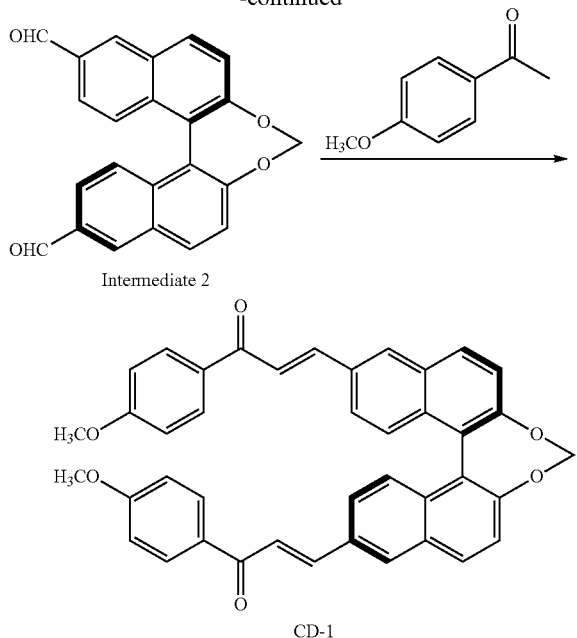

Intermediate 2

CD-1

(Synthesis of Intermediate 1)

65.0 g of (R)-binaphthol (manufactured by KANTO CHEMICAL CO., INC.) and 500 mL of butyl acetate (manufactured by Wako Pure Chemical Industries, Ltd.) were placed in a three-neck flask (capacity: 2 L) to obtain a mixed solution. The temperature of the mixed solution was lowered to 0° C., 100 g of bromine (manufactured by Wako Pure Chemical Industries, Ltd.) was added dropwise thereto, and the obtained reaction solution was stirred for 5 hours. After completion of the stirring, the reaction solution was washed with sodium hydrogen sulfite water (21.7 g of sodium hydrogen sulfite (manufactured by Wako Pure Chemical Industries, Ltd.) and 290 mL of water), water (325 mL), and sodium hydrogen carbonate water (13.0 g of sodium hydrogen carbonate (manufactured by Wako Pure Chemical Industries, Ltd.) and 300 mL of water) respectively, the obtained solution was dried over magnesium sulfate, and then the solvent was evaporated from the solution under reduced pressure.

The obtained residue, 80.2 g of N,N-dimethylformamide (DMF) (manufactured by Wako Pure Chemical Industries, Ltd.), 78.0 g of potassium carbonate (manufactured by Wako Pure Chemical Industries, Ltd.), and 75 g of butyl acetate (manufactured by Wako Pure Chemical Industries, Ltd.) were placed in a three-neck flask to obtain a mixed solution. 43.5 g of dibromomethane (manufactured by Wako Pure Chemical Industries, Ltd.) was added dropwise to the mixed solution, and the reaction solution was stirred at 90° C. for 4 hours. The temperature of the obtained reaction solution was lowered to room temperature, and inorganic salts in the reaction solution were filtered off. After adding 170 mL of ethyl acetate (manufactured by Wako Pure Chemical Industries, Ltd.) to the obtained filtrate, 550 mL of methanol (manufactured by Wako Pure Chemical Industries, Ltd.) was added thereto at 45° C., and the resulting solid was collected by filtration. The solid collected by filtration was blast-dried at 40° C. for 12 hours, thereby obtaining an intermediate 1 (66.0 g, yield: 75%).

(Synthesis of Intermediate 2)

The intermediate 1 (3.00 g) was placed in a three-neck flask (capacity: 300 mL), and 65 mL of tetrohydrofuran (THF) (manufactured by Wako Pure Chemical Industries, Ltd.) was further added thereto under a nitrogen atmosphere to obtain a mixed solution. The temperature of the mixed solution was lowered to −78° C., and 17 mL of a 1.6 M normal butyllithium hexane solution (manufactured by Wako Pure Chemical Industries, Ltd.) was added dropwise to the mixed solution. After stirring the obtained reaction solution at −78° C. for 4 hours, 3.5 mL of DMF (manufactured by Wako Pure Chemical Industries, Ltd.) was added dropwise to the reaction solution, and the reaction solution was further stirred at −60° C. for 30 minutes. 200 mL of water and 2 mL of a 35% hydrochloric acid water (manufactured by Wako Pure Chemical Industries, Ltd.) were placed in an Erlenmeyer flask (capacity: 1 L), the temperature thereof was lowered to 0° C., and then the reaction solution was poured thereto. 170 mL of ethyl acetate (manufactured by Wako Pure Chemical Industries, Ltd.) was further added to the Erlenmeyer flask, the obtained solution was washed with saturated saline and dried over magnesium sulfate, and then the solvent was evaporated from the obtained solution under reduced pressure. The obtained residue was purified by silica gel column chromatography using ethyl acetate/normal hexane (volume ratio: 4:6) as a developing solvent, and the solvent was evaporated from the separated solution under reduced pressure, thereby obtaining an intermediate 2 (1.27 g, yield: 54%).

(Synthesis of Compound CD-1)

The intermediate 2 (4.50 g), 4.20 g of 4-methoxyacetophenone (manufactured by Wako Pure Chemical Industries, Ltd.), and 135 mL of THF (manufactured by Wako Pure Chemical Industries, Ltd.) were placed in a three-neck flask (capacity: 300 mL) to obtain a mixed solution. The mixed solution was cooled to 0° C., 4.90 g of a 28% sodium methoxide methanol solution (manufactured by Tokyo Chemical Industry Co., Ltd.) was added dropwise to the mixed solution, and the obtained reaction solution was stirred at 0° C. for 3.5 hours. 10 mL of IN hydrochloric acid, 30 mL of ethyl acetate, and 90 mL of water were added to the reaction solution, the obtained solution was washed with saturated saline and dried over magnesium sulfate, and then the solvent was evaporated from the obtained solution under reduced pressure. The obtained crude product was purified by silica gel column chromatography using ethyl acetate/normal hexane (volume ratio: 4:6) as a developing solvent, and the solvent was evaporated from the separated solution under reduced pressure, thereby obtaining a compound CD-1 (1.60 g, yield: 20%).

The results of identification of the compound CD-1 by $^1$H nuclear magnetic resonance (NMR) (deuterated solvent: DMSO-$d_6$) are shown below.

$^1$H NMR (DMSO-$d_6$): δ=8.52 (2H, s), 8.22 (6H, m), 8.07 (4H, m), 7.89 (2H, d), 7.66 (2H, d), 7.38 (2H, d), 7.10 (4H, d), 5.78 (2H, s), 3.87 (6H, s)

Compounds CD-2 to CD-16 were synthesized with reference to the above-described method.

HTPs of the obtained compounds CD-1 to CD-16 were evaluated as described later.

In addition, as comparative compounds, compounds CE-1 to CE-4 were synthesized.

The method of synthesizing each compound was performed with reference to "Experimental Chemistry Course 16, 5th edition" pp. 35 to 70, edited by The Chemical Society of Japan.

The compound CE-1 was a compound (R)-XII disclosed in Anna Kickova et al. Chemical Papers, 2013, vol. 67, pp.

101 to 109, and was synthesized according to the method disclosed in Anna Kickova et al. Chemical Papers, 2013, vol. 67, pp. 101 to 109.

The compound CE-2 was a compound described in Molecular Crystals and Liquid Crystals (2004, vol. 425, pp. 153 to 158), and was synthesized according to the method described in the above reference.

The compound CE-4 was a compound described in Advanced Synthesis & Catalysis (2004, vol. 346, pp. 1728 to 1732), and was synthesized according to the method described in the above reference.

The structures of the compounds CD-1 to CD-16, and CE-1 to CE-4 are shown below.

CD-1

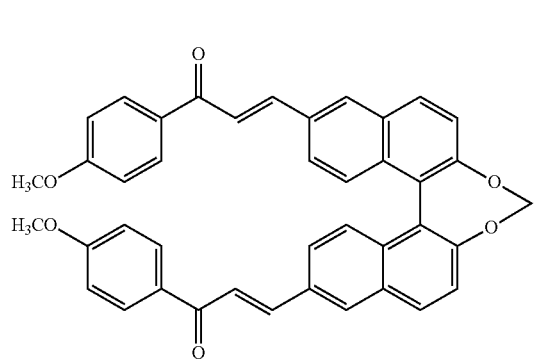

CD-2

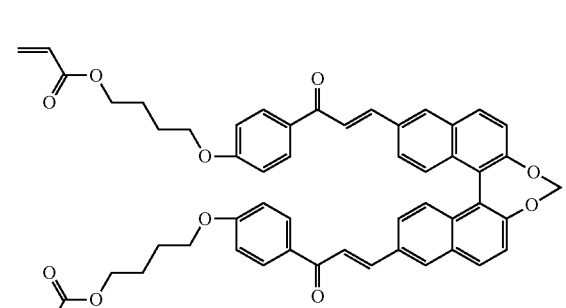

CD-3

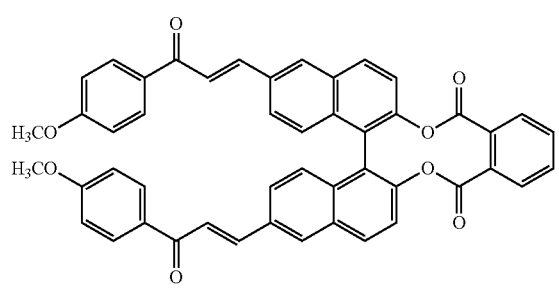

CD-4

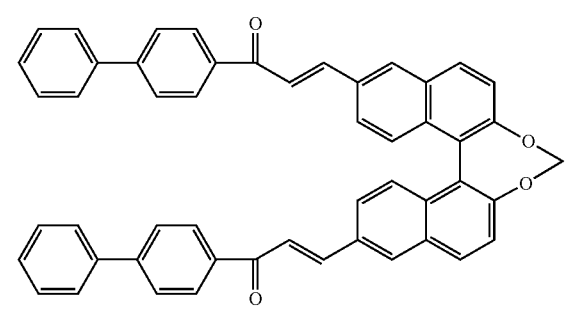

CD-5

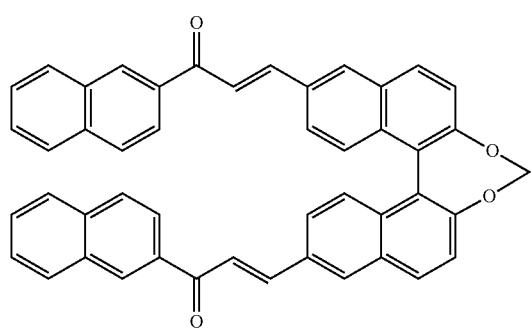

CD-6

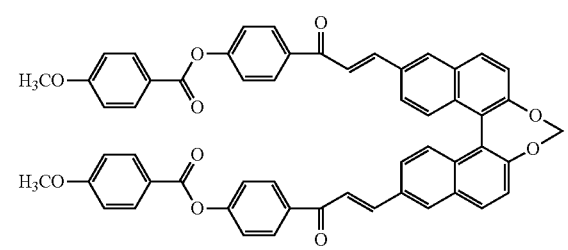

CD-7

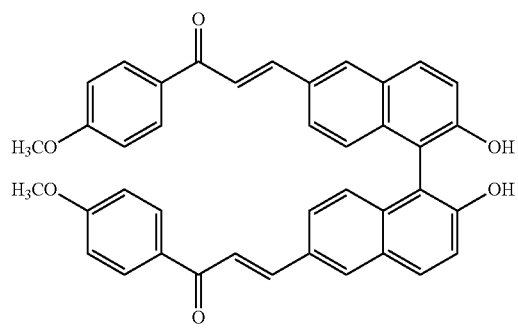

CD-8

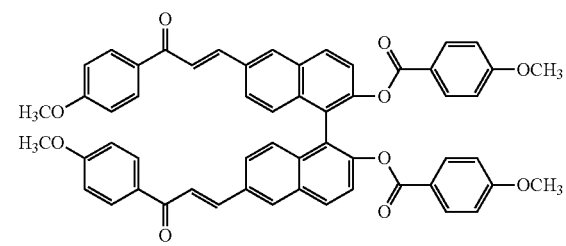

-continued
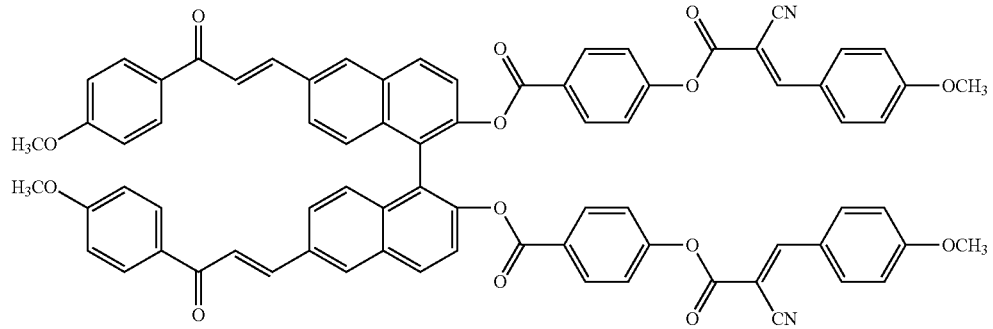
CD-9
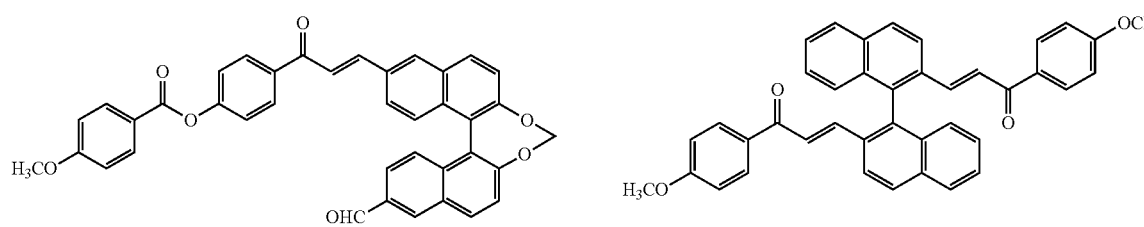
CD-10
CD-11
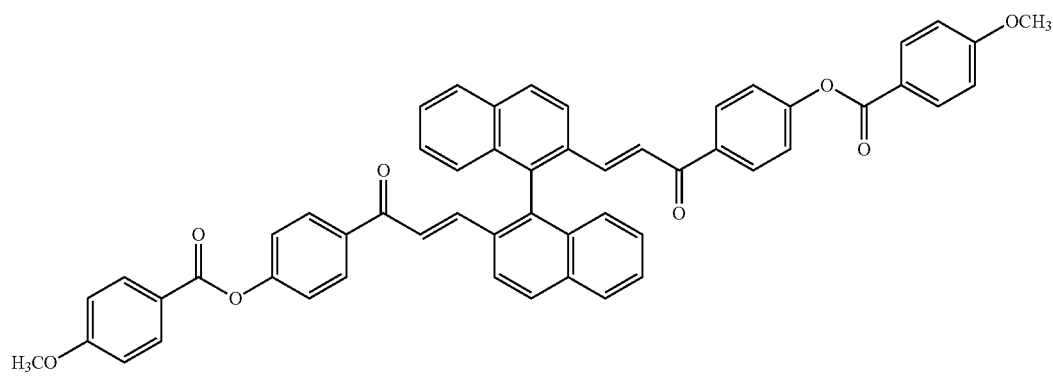
CD-12
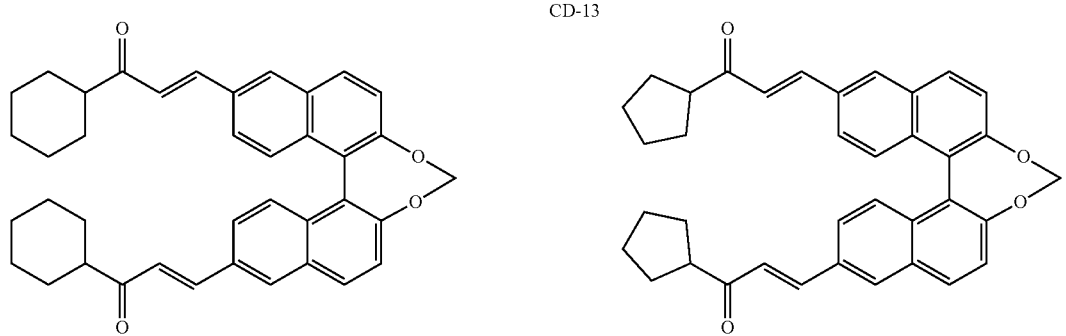
CD-13
CD-14
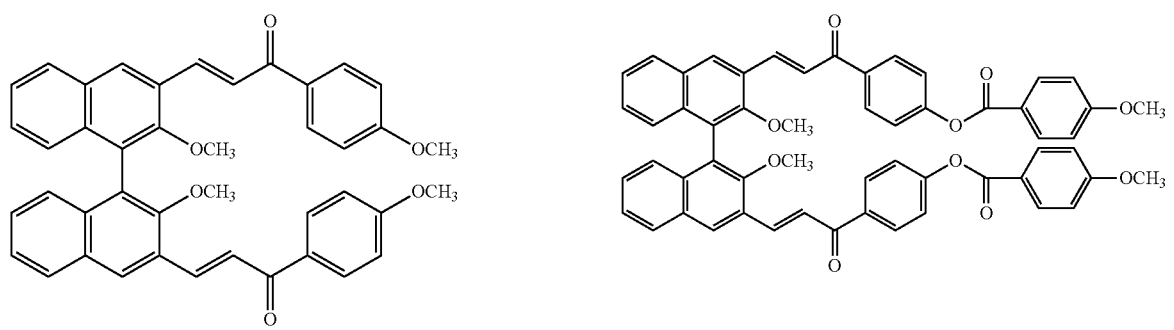
CD-15
CD-16

-continued

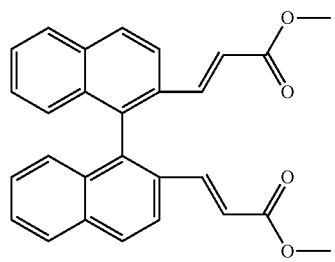

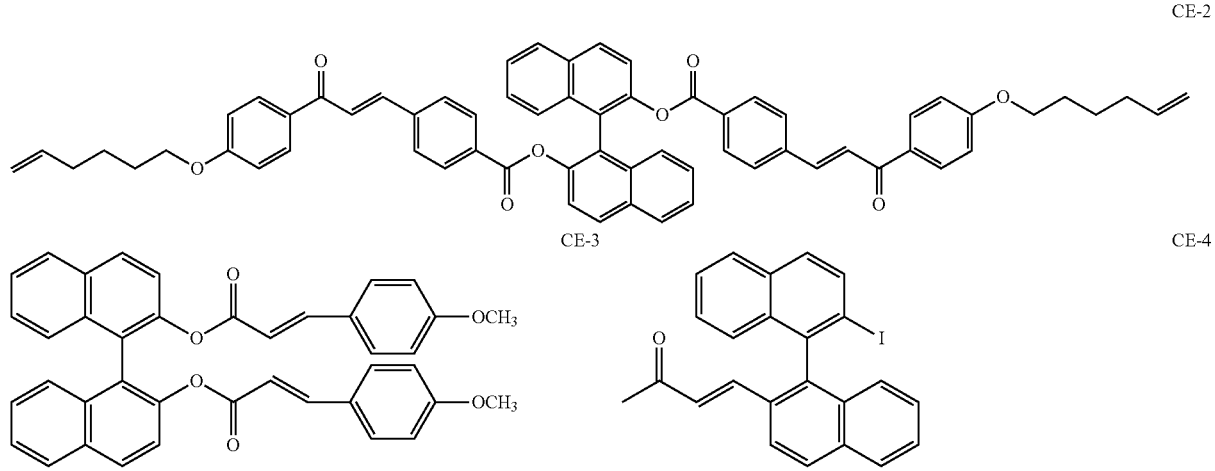

[Evaluation]
<Evaluation of Helical Twisting Power (HTP) and Rate of Change in HTP Due to Exposure>
Various compositions for evaluation were prepared with the formulations shown below.
  Any one of compounds CD-1 to CD-16 or CE-1 to CE-4: 5 parts by mass
  Liquid crystalline compound LC-1 shown below: 100 parts by mass
  Solvent (methyl ethyl ketone/cyclohexanone=90/10 (mass ratio)): amount at which the concentration of solid contents of the composition is 30% by mass 40 μL of the above-described composition was spin-coated on the rubbing-treated surface of the alignment film under the conditions of 1500 rpm and 10 seconds, and then the substrate was heat-dried at 90° C. for 1 minute to form a composition layer.

Regarding the obtained composition layer, the central reflection wavelength was measured at room temperature (23° C.) using a microscope (ECLIPSE E600-POL manufactured by Nikon Corporation) and a spectrophotometer (UV-3100(PC) manufactured by Shimadzu Corporation), and HTP (initial HTP) was calculated according to the following expression.

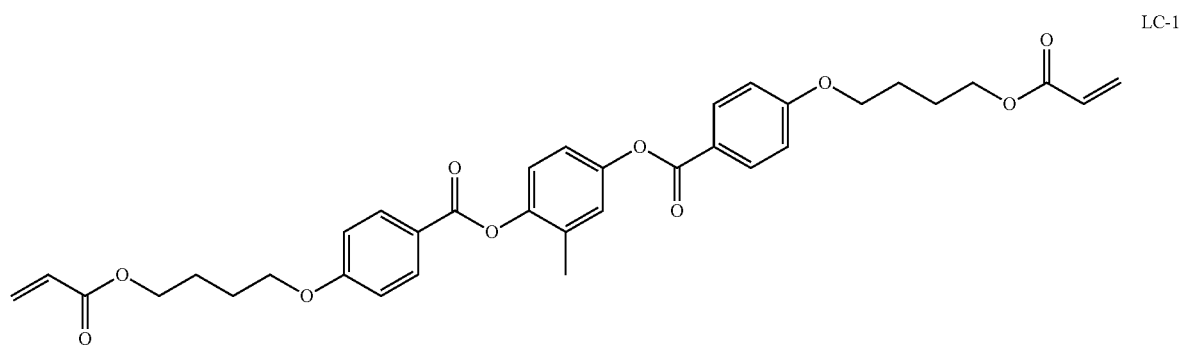 [SMILES: C=CC(=O)OCCCCOc1ccc(C(=O)Oc2ccc(OC(=O)c3ccc(OCCCCOC(=O)C=C)cc3)c(C)c2)cc1]

(Production of Liquid Crystal Layer 1)
A polyimide alignment film material SE-130 (manufactured by Nissan Chemical Corporation) was applied to a washed glass substrate to form a coating film. After firing the obtained coating film, the coating film was subjected to a rubbing treatment to produce a substrate with an alignment film.

HTP [μm$^{-1}$]=(average refractive index of liquid crystalline compound)/{(concentration (mass %) of chiral compound with respect to liquid crystalline compound)×(central reflection wavelength)}

HTP was calculated on the assumption that the average refractive index of the liquid crystalline compound was 1.55.

Furthermore, after exposing the composition layer to light having a wavelength of 365 nm (exposure amount: 150 mJ/cm$^2$), the central reflection wavelength was measured again, and HTP after exposure was calculated in the same manner as the initial HTP using the above-described calculation expression. From the obtained initial HTP and HTP after exposure, the rate of change in HTP was calculated according to the following expression.

Rate of change in HTP[%]=|{(initial HTP)−(HTP after exposure)}/(initial HTP)×100|

The initial HTP and the rate of change in HTP were evaluated based on the following standard, respectively. In both standards, evaluation A is the most preferable.

(Evaluation Standard of Initial HTP)
A: initial HTP was 90 μm$^{-1}$ or more.
B: initial HTP was 80 μm$^{-1}$ or more and less than 90 μm$^{-1}$.
C: initial HTP was 60 μm$^{-1}$ or more and less than 80 μm$^{-1}$.
D: initial HTP was 40 μm$^{-1}$ or more and less than 60 μm$^{-1}$.
E: initial HTP was less than 40 μm$^{-1}$.

(Evaluation Standard of Rate of Change in HTP)
A: rate of change in HTP was 60% or more.
B: rate of change in HTP was 50% or more and less than 60%.
C: rate of change in HTP was 40% or more and less than 50%.
D: rate of change in HTP was 30% or more and less than 40%.
E: rate of change in HTP was less than 30%.

[Result]

Evaluation results of Examples using the compositions produced by adding each compound are shown in the following table.

In the table, the column of "General Formula (2)" indicates a position of the group represented by General Formula (2) in $X^1$ to $X^6$, in a case where the compound used in each example corresponds to General Formula (1).

The column of "$A^1$" indicates whether or not $A^1$ in the group represented by General Formula (2) in $X^1$ to $X^6$ is an aromatic hydrocarbon ring group. A case where this requirement is satisfied is indicated as A, and a case where this requirement is not satisfied is indicated as B.

The column of "Linking ring of $X^1$ and $X^2$" indicates whether or not $X^1$ and $X^2$ are bonded to each other to form a ring, in a case where the compound used in each example corresponds to General Formula (1). A case where this requirement is satisfied is indicated as A, and a case where this requirement is not satisfied is indicated as B.

The column of "General Formula (A), k≥2" indicates whether or not the requirement of "at least one of $X^1$ or $X^2$ is the group represented by General Formula (A) and k in General Formula (A) is 2 or more" is satisfied, in a case where a compound indicated as B in the column of "Linking ring of $X^1$ and $X^2$" has the group represented by General Formula (2) at at least one of $X^3$, $X^4$, $X^5$, or $X^6$. A case where this requirement is satisfied is indicated as A, and a case where this requirement is not satisfied is indicated as B.

The column of "General Formula (3)" indicates whether or not the group represented by General Formula (2) in $X^1$ to $X^6$ is the group represented by General Formula (3), in a case where the compound used in each example corresponds to General Formula (1). A case where this requirement is satisfied is described as A, and a case where this requirement is not satisfied is described as B.

TABLE 1

| | Compound | General Formula (2) | $A^1$ | Linking ring of $X^1$ and $X^2$ | General Formula (A), k ≥ 2 | General Formula (3) | Initial HTP | Rate of change in HTP |
|---|---|---|---|---|---|---|---|---|
| Example 1 | CD-1 | $X^5$, $X^6$ | A | A | — | B | B | A |
| Example 2 | CD-2 | $X^5$, $X^6$ | A | A | — | B | B | A |
| Example 3 | CD-3 | $X^5$, $X^6$ | A | A | — | B | B | A |
| Example 4 | CD-4 | $X^5$, $X^6$ | A | A | — | A | A | A |
| Example 5 | CD-5 | $X^5$, $X^6$ | A | A | — | B | B | A |
| Example 6 | CD-6 | $X^5$, $X^6$ | A | A | — | A | A | A |
| Example 7 | CD-7 | $X^5$, $X^6$ | A | B | B | B | D | B |
| Example 8 | CD-8 | $X^5$, $X^6$ | A | B | B | B | D | B |
| Example 9 | CD-9 | $X^5$, $X^6$ | A | B | A | B | C | B |
| Example 10 | CD-10 | $X^5$ | A | A | — | A | E | D |
| Example 11 | CD-11 | $X^1$, $X^2$ | A | B | — | B | D | B |
| Example 12 | CD-12 | $X^1$, $X^2$ | A | B | — | A | C | B |
| Example 13 | CD-13 | $X^5$, $X^6$ | B | A | — | B | C | C |
| Example 14 | CD-14 | $X^5$, $X^6$ | B | A | — | B | C | C |
| Example 15 | CD-15 | $X^3$, $X^4$ | A | B | B | B | D | B |
| Example 16 | CD-16 | $X^3$, $X^4$ | A | B | B | A | C | B |
| Comparative Example 1 | CE-1 | — | — | — | — | — | E | E |
| Comparative Example 2 | CE-2 | — | — | — | — | — | C | E |
| Comparative Example 3 | CE-3 | — | — | — | — | — | D | E |
| Comparative Example 4 | CE-4 | — | — | — | — | — | D | E |

From the results shown in the table, it was confirmed that the compound according to the embodiment of the present invention was excellent in the rate of change in HTP due to exposure.

In addition, in a case where at least one of $X^1$, $X^3$, or $X^5$ was the group represented by General Formula (2) and at least one of $X^2$, $X^4$, or $X^6$ was the group represented by General Formula (2), it was found that each of the initial HTP and the rate of change in HTP was more excellent (comparison of Example 6 with Example 10).

In a case where $A^1$ in the group represented by General Formula (2) in $X^1$ to $X^6$ was an aromatic hydrocarbon ring group, it was found that each of the initial HTP and the rate of change in HTP was more excellent (comparison of Example 1 with Examples 13 and 14).

In a case where $X^1$ and $X^2$ were bonded to each other to form a ring, it was found that each of the initial HTP and the rate of change in HTP was more excellent (comparison of Examples 1 and 3 with Examples 7 to 9).

In a case where at least one of $X^3$, $X^4$, $X^5$, or $X^6$ was the group represented by General Formula (2) and a case where, in a case where $X^1$ and $X^2$ were not bonded to each other to form a ring, at least one of $X^1$ or $X^2$ was the group represented by General Formula (A) and k in General Formula (A) was 2 or more, it was found that the initial HTP was more excellent (comparison of Example 9 with Examples 7 and 8).

In a case where the group represented by General Formula (2) in $X^1$ to $X^6$ was the group represented by General Formula (3), it was found that the initial HTP was more excellent (comparison of Examples 4 and 6 with Examples 1 to 3 and 5, comparison of Example 12 with Example 11, and comparison of Example 16 with Example 15).

[Production of Reflective Film]
<Preparation of Liquid Crystal Composition>

A liquid crystal composition was prepared with the formulation shown below.

Compound CD-1: 5 parts by mass
Liquid crystalline compound LC-1 shown above: 100 parts by mass
Surfactant S-1 shown below: 0.1 parts by mass
Polymerization initiator X shown below: 3 parts by mass
Solvent (methyl ethyl ketone/cyclohexanone=90:10 (mass ratio)): amount at which the concentration of solid contents of the composition is 30% by mass The surfactant S-1 is a compound described in JP5774518B, and has the following structure.

Polymerization initiator X: IRGACURE 907 (manufactured by BASF)

(Production of Reflective Film)

A polyimide alignment film material SE-130 (manufactured by Nissan Chemical Corporation) was applied to a washed glass substrate to form a coating film. After firing the obtained coating film, the coating film was subjected to a rubbing treatment to produce a substrate with an alignment film. 40 μL of the above-described liquid crystal composition was spin-coated on the rubbing-treated surface of the alignment film under the conditions of a rotation speed of 1500 rpm for 10 seconds to form a composition layer. Thereafter, the composition layer was dried (aged) at 90°C for 1 minute, thereby aligning the liquid crystalline compound in the composition layer (in other words, obtaining a composition layer in a state of the cholesteric liquid crystalline phase).

Next, the composition layer in which the liquid crystalline compound had been aligned was irradiated with light, which is emitted from a light source (2UV Transilluminator manufactured by UVP Inc.) and has a wavelength of 365 nm, at an irradiation intensity of 0.4 mW/cm² for 1 minute through a mask having an opening portion (corresponding to the treatment of changing HTP of CD-1). Due to the difference between the opening portion and the non-opening portion of the mask, the composition layer was in a state of having a portion irradiated with light having a wavelength of 365 nm and a portion not irradiated with light.

Subsequently, in a state of removing the mask, the composition layer was subjected to a curing treatment by irradiation with ultraviolet rays (310 nm) at an irradiation amount of 500 mJ/cm² under a nitrogen atmosphere at 25° C., thereby obtaining a reflective film (corresponding to a layer obtained by immobilizing the cholesteric liquid crystalline phase).

In the obtained reflective film, it was found that the selective reflection wavelengths differed between the portion irradiated with light having a wavelength of 365 nm and the portion not irradiated (that the helical pitches of the cholesteric layer differed therebetween).

(S-1)

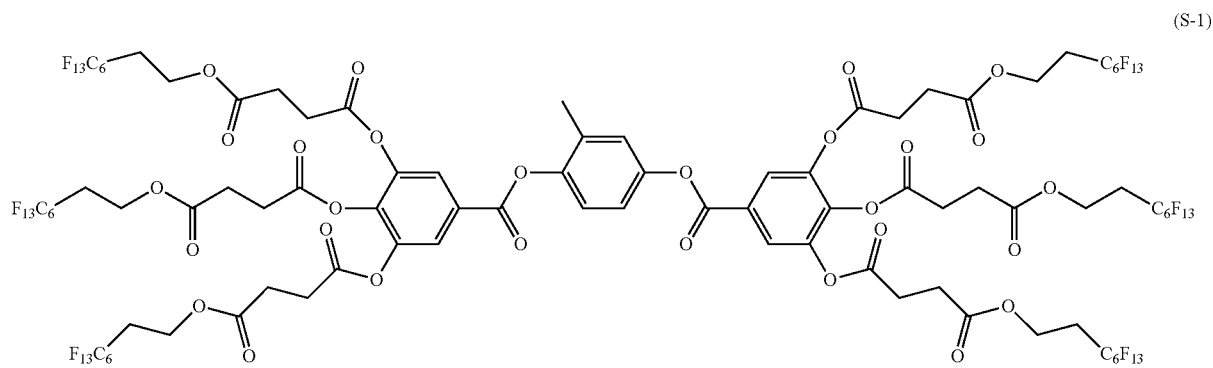

What is claimed is:

1. A compound represented by General Formula (1),

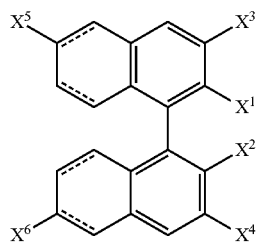

in General Formula (1), $X^1$ to $X^6$ each independently represent a hydrogen atom or a substituent, at least one of $X^1$, $X^2$, $X^3$, $X^4$, $X^5$, or $X^6$ represents a group represented by General Formula (2), and a plurality of groups selected from $X^1$ to $X^6$ may be bonded to each other to form a ring;

$$(R^1)_n\text{-}A^1\text{-}C^x O\text{---}CH\!=\!CH\text{---}* \qquad (2)$$

in General Formula (2), $A^1$ represents a hydrocarbon ring group or a heterocyclic group, n represents an integer of 0 or more, $R^1$ represents a substituent, * represents a bonding position to a fused ring in General Formula (1), and a carbon atom $C^x$ is bonded to a carbon atom in $A^1$.

2. The compound according to claim 1, wherein $A^1$ represents an aromatic hydrocarbon ring group or an aromatic heterocyclic group.

3. The compound according to claim 1, wherein $X^1$ and $X^2$ are bonded to each other to form a ring.

4. The compound according to claim 1, wherein at least one of $X^1$, $X^3$, or $X^5$ represents the group represented by General Formula (2), and at least one of $X^2$, $X^4$, or $X^6$ represents the group represented by General Formula (2).

5. The compound according to claim 1, wherein at least one of $X^3$, $X^4$, $X^5$, or $X^6$ represents the group represented by General Formula (2), and at least one of $X^1$ or $X^2$ represents a group represented General Formula (A), $$R^3\text{-}(A^4\text{-}Z^2)_k\text{---}* \qquad (A)$$

in General Formula (A), k represents an integer of 2 or more, $R^3$ represents a hydrogen atom or a substituent, $Z^2$ represents a single bond, —O—, —S—, —CH$_2$O—, —CO—, —COO—, —CO—S—, —O—CO—O—, —CO—NH—, —CH$_2$S—, —CF$_2$O—, —CF$_2$S—, —CH=CH—COO—, —CH=CH—OCO—, —OCO—C(CN)=CH—, —COO—CH$_2$CH$_2$—, —OCO—CH$_2$CH$_2$—, —COO—CH$_2$—, —OCO—CH$_2$—, —CH=CH—, —N=N—, —CH=N—N=CH—, —CF=CF—, or —C≡C—, $A^4$ represents a hydrocarbon ring group or a heterocyclic group, and * represents a bonding position to the fused ring in General Formula (1).

6. The compound according to claim 1, wherein the group represented by General Formula (2) is a group represented by General Formula (3), $$R^2\text{-}(A^3\text{-}Z^1)_m\text{-}A^2\text{-}C^xO\text{---}CH\!=\!CH\text{---}* \qquad (3)$$

in General Formula (3), m represents an integer of 1 or 2, $R^2$ represents a hydrogen atom or a substituent, $Z^1$ represents a single bond, —O—, —S—, —CH$_2$O—, —CO—, —COO—, —CO—S—, —O—CO—O—, —CO—NH—, —CH$_2$S—, —CF$_2$O—, —CF$_2$S—, —CH=CH—COO—, —CH=CH—OCO—, —OCO—C(CN)=CH—, —COO—CH$_2$CH$_2$—, —OCO—CH$_2$CH$_2$—, —COO—CH$_2$—, —OCO—CH$_2$—, —CH=CH—, —N=N—, —CH=N—N=CH—, —CF=CF—, or —C≡C—, $A^2$ and $A^3$ each independently represent a hydrocarbon ring group or a heterocyclic group, * represents a bonding position to the fused ring in General Formula (1), and a carbon atom $C^x$ is bonded to a carbon atom in $A^2$.

7. A composition comprising:
the compound according to claim 1.

8. The composition according to claim 7, further comprising:
a liquid crystalline compound.

9. The composition according to claim 8, wherein the liquid crystalline compound has two polymerizable groups.

10. A cured product obtained by curing the composition according to claim 7.

11. An optically anisotropic body obtained by curing the composition according to claim 8.

12. A reflective film obtained by curing the composition according to claim 8.

* * * * *